(12) United States Patent
Andree et al.

(10) Patent No.: US 6,624,120 B1
(45) Date of Patent: Sep. 23, 2003

(54) SUBSTITUTED HERBICIDAL PHENYLURACILS

(75) Inventors: Roland Andree, Langenfeld (DE); Hans-Georg Schwarz, Langenfeld (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,153

(22) PCT Filed: Jun. 5, 2000

(86) PCT No.: PCT/EP00/05113

§ 371 (c)(1), (2), (4) Date: Dec. 13, 2001

(87) PCT Pub. No.: WO00/78734

PCT Pub. Date: Dec. 28, 2000

(30) Foreign Application Priority Data

Jun. 17, 1999 (DE) .......................... 199 27 612

(51) Int. Cl.$^7$ .................. C07D 239/54; A01N 43/54
(52) U.S. Cl. .................. 504/243; 544/311; 544/312; 544/313; 544/314
(58) Field of Search .................. 544/311, 312, 544/313, 314; 504/243

(56) References Cited

U.S. PATENT DOCUMENTS

| | | | |
|---|---|---|---|
| 4,859,229 A | 8/1989 | Wenger et al. | 71/92 |
| 4,979,982 A | 12/1990 | Brouwer et al. | 71/92 |
| 5,084,084 A | 1/1992 | Satow et al. | 71/92 |
| 5,116,404 A | 5/1992 | Ishii et al. | 71/92 |
| 5,127,935 A | 7/1992 | Satow et al. | 71/92 |
| 5,134,144 A | 7/1992 | Brouwer et al. | 514/274 |
| 5,154,755 A | 10/1992 | Satow et al. | 71/92 |
| 5,169,430 A | 12/1992 | Strunk et al. | 71/92 |
| 5,183,492 A | 2/1993 | Suchy et al. | 504/243 |
| 5,266,554 A | 11/1993 | Suchy et al. | 504/243 |
| 5,280,010 A | 1/1994 | Enomoto et al. | 504/243 |
| 5,356,863 A | 10/1994 | Satow et al. | 504/243 |
| 5,486,610 A | 1/1996 | Strunk et al. | 544/311 |
| 5,567,670 A | 10/1996 | Amuti et al. | 504/230 |
| 5,593,945 A | 1/1997 | Andree et al. | 504/243 |
| 5,602,077 A | 2/1997 | Amuti et al. | 504/243 |
| 5,681,794 A | 10/1997 | Andree et al. | 504/243 |
| 6,110,870 A | 8/2000 | Andree et al. | 504/243 |

FOREIGN PATENT DOCUMENTS

| | | |
|---|---|---|
| DE | 196 04 229 | 8/1996 |
| EP | 260 621 | 3/1988 |
| EP | 563 384 | 10/1993 |
| WO | 96/35679 | 11/1996 |
| WO | 00/02866 | 1/2000 |

OTHER PUBLICATIONS

J. Heterocycl. Chem. Jun. 9, 1972, pp. 513–522, Albert W. Lutz and Susan H. Trotto, "Novel 6–(Trifluoromethyl)cytosines and 6–(Trifluoromethyl)uracils".

*Primary Examiner*—John M. Ford
(74) *Attorney, Agent, or Firm*—Richard E. L. Henderson; Raymond J. Harmuth

(57) ABSTRACT

The invention relates to novel substituted phenyluracils of the general formula (I)

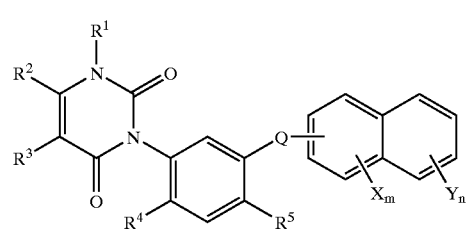

in which
m, n, Q, $R^1$, $R^2$, $R^3$, $R^4$, $R^5$, X and Y are each as defined in the description,
to processes for their preparation, to novel intermediates and to their use as herbicides.

9 Claims, No Drawings

SUBSTITUTED HERBICIDAL PHENYLURACILS

The invention relates to novel substituted phenyluracils, to processes and novel intermediates for their preparation and to their use as herbicides.

Certain substituted aryluracils are already known from the (patent) literature (cf. EP-A-255 047, EP-A-260 621, EP-A-408 382, EP-A-438 209, EP-A-473 551, EP-A-517 181, EP-A-563 384, WO-A-91/00278, WO-A-91/07393, WO-A-93/14073, U.S. Pat. No. 4,979,982, U.S. Pat No. 5,084,084, U.S. Pat. No. 5,127,935, U.S. Pat. No. 5,154,755, U.S. Pat. No. 5,169,430, U.S. Pat. No. 5,486,610, U.S. Pat. No. 5,356,863). However, these compounds have hitherto not attained any particular importance.

This invention, accordingly, provides novel substituted phenyluracils of the general formula (I)

$$\text{(I)}$$

in which
m represents 0, 1, 2 or 3,
n represents 0, 1, 2, 3 or 4,
Q represents O (oxygen), S (sulphur), SO, $SO_2$, NH or N(alkyl),
$R^1$ represents hydrogen, amino or optionally substituted alkyl,
$R^2$ represents carboxyl, cyano, carbamoyl, thiocarbamoyl or in each case optionally substituted alkyl or alkoxycarbonyl,
$R^3$ represents hydrogen, halogen or optionally substituted alkyl,
$R^4$ represents hydrogen, cyano, carbamoyl, thiocarbamoyl or halogen,
$R^5$ represents cyano, carbamoyl, thiocarbamoyl, halogen or in each case optionally substituted alkyl or alkoxy,
X represents hydroxyl, mercapto, amino, nitro, formyl, cyano, carboxyl, carbamoyl, thiocarbamoyl, halogen, sulphonyl, halogenosulphonyl, or represents in each case optionally substituted alkyl, alkoxy, alkylthio, alkylsulphinyl, alkylsulphonyl, alkylamino, dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, alkylcarbonylamino, alkoxycarbonylamino, alkylsulphonylamino, alkenyl, alkenyloxy, alkenyloxycarbonyl, alkenylcarbonyloxy, alkinyl, alkinyloxy, alkinyloxycarbonyl, alkinylcarbonyloxy or arylcarbonyloxy, and
Y represents hydroxyl, mercapto, amino, nitro, formyl, cyano, carboxyl, carbamoyl, thiocarbamoyl, halogen, sulphonyl, halogenosulphonyl, or represents in each case optionally substituted alkyl, alkoxy, alkylthio, alkylsulphinyl, alkylsulphonyl, alkylamino, dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, alkylcarbonylamino, alkoxycarbonylamino, alkylsulphonylamino, alkenyl, alkenyloxy, alkenyloxycarbonyl, alkenylcarbonyloxy, alkinyl, alkinyloxy, alkinyloxycarbonyl, alkinylcarbonyloxy or arylcarbonyloxy, where, in the case that m and/or n are greater than 1, X and Y in the individual compounds possible in each case have identical or different meanings from those given, which is to say that X and Y may be identical or different, and salts of compounds of the formula (I).

Preferred substituents or ranges of the radicals present in the formulae given above and below are defined below.

m preferably represents 0, 1 or 2.
n preferably represents 0, 1, 2 or 3.
Q preferably represents O (oxygen), S (sulphur), SO, $SO_2$, NH or $N(C_1-C_4\text{-alkyl})$.
$R^1$ preferably represents hydrogen, amino or represents optionally cyano-, halogen- or $C_1-C_3$-alkoxy-substituted alkyl having 1 to 4 carbon atoms.
$R^2$ preferably represents carboxyl, cyano, carbamoyl, thiocarbamoyl or represents in each case optionally cyano-, halogen- or $C_1-C_3$-alkoxy-substituted alkyl or alkoxycarbonyl having in each case 1 to 4 carbon atoms.
$R^3$ preferably represents hydrogen, halogen or represents optionally cyano-, halogen- or $C_1-C_3$-alkoxy-substituted alkyl having 1 to 4 carbon atoms.
$R^4$ preferably represents hydrogen, cyano, fluorine or chlorine.
$R^5$ preferably represents cyano, carbamoyl, thiocarbamoyl, halogen or represents in each case optionally halogen-substituted alkyl or alkoxy having in each case 1 to 4 carbon atoms.
X preferably represents hydroxyl, mercapto, amino, nitro, formyl, cyano, carboxyl, carbamoyl, thiocarbamoyl, halogen, sulphonyl, halogenosulphonyl, represents in each case optionally cyano-, carboxyl-, carbamoyl-, halogen-, $C_1-C_4$-alkoxy-, $C_1-C_4$-alkylthio-, $C_1-C_4$-alkylsulphinyl-, $C_1-C_4$-alkylsulphonyl-, $C_1-C_4$-alkylcarbonyl-, $C_1-C4$-alkoxy-carbonyl-, $C_2-C_4$-alkenyloxy-carbonyl-, $C_2-C_4$-alkinyloxy-carbonyl-, $C_1-C_4$-alkylaminocarbonyl-, di-$(C_1-C_4$-alkyl)-amino-carbonyl-, phenoxycarbonyl-, benzyloxycarbonyl-, phenylaminocarbonyl- or benzylaminocarbonyl-substituted alkyl, alkoxy, alkylthio, alkylsulphinyl, alkylsulphonyl or alkylamino having in each case 1 to 6 carbon atoms, represents dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, alkylcarbonylamino, alkoxycarbonylamino, alkyl-sulfonylamino, bis-alkylsulfonyl-amino or N-alkylcarbonyl-N-alkylsulphonyl-amino having in each case 1 to 6 carbon atoms in the alkyl groups, represents in each case optionally cyano-, carboxyl-, carbamoyl-, halogen-, $C_1-C_4$-alkoxycarbonyl-, $C_1-C_4$-alkylamino-carbonyl- or di-$(C_1-C_4$-alkyl)-amino-carbonyl-substituted alkenyl, alkenyloxy, alkenyloxycarbonyl, alkenylcarbonyloxy, alkinyl, alkinyloxy, alkinyloxycarbonyl or alkinylcarbonyloxy having in each case 2 to 6 carbon atoms in the alkenyl or alkinyl groups, or represents benzyloxy.

Y preferably represents hydroxyl, mercapto, amino, nitro, formyl, cyano, carboxyl, carbamoyl, thiocarbamoyl, halogen, sulphonyl, halogenosulphonyl, represents in each case optionally cyano-, carboxyl-, carbamoyl-, halogen-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkylcarbonyl-, $C_1$–$C_4$-alkoxy-carbonyl-, $C_2$-$C_4$-alkenyloxy-carbonyl-, $C_2$-$C_4$-alkinyloxy-carbonyl-, aminocarbonyl-, $C_1$–$C_4$-alkylaminocarbonyl-, di-($C_1$–$C_4$-alkyl)-amino-carbonyl-, phenoxycarbonyl-, benzyloxycarbonyl-, phenylaminocarbonyl- or benzylaminocarbonyl- substituted alkyl, alkoxy, alkylthio, alkylsulphinyl, alkylsulphonyl or alkylamino having in each case 1 to 6 carbon atoms, represents dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkyl-aminocarbonyloxy, alkylcarbonylamino, alkoxycarbonylamino, alkyl-sulfonylamino, bis-alkylsulfonyl-amino or N-alkylcarbonyl-N-alkylsulphonyl-amino having in each case 1 to 6 carbon atoms in the alkyl groups, represents in each case optionally cyano-, carboxyl-, carbamoyl-, halogen-, $C_1$–$C_4$-alkoxycarbonyl-, $C_1$–$C_4$-alkylamino-carbonyl- or di-($C_1$–$C_4$-alkyl)-aminocarbonyl-substituted alkenyl, alkenyloxy, alkenyloxycarbonyl, alkenylcarbonyloxy, alkinyl, alkinyloxy, alkinyloxycarbonyl or alkinyl-carbonyloxy having in each case 2 to 6 carbon atoms in the alkenyl or alkinyl groups, or represents benzyloxy.

The invention also preferably provides the sodium, potassium, magnesium, calcium, ammonium, $C_1$–$C_4$-alkyl-ammonium, di-($C_1$–C4-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I), in which m, n, Q, $R^1$, $R^2$, $R^3$, $R^4$, $R^5$, X and Y have the preferred meanings given above—insofar as the compounds of the formula (I) contain hydrogen atoms attached to O or S.

m particularly preferably represents 0 or 1.

n particularly preferably represents 0, 1 or 2.

Q particularly preferably represents O (oxygen) or S (sulphur).

$R^1$ particularly preferably represents hydrogen, amino or represents in each case optionally cyano-, fluorine-, chlorine-, methoxy- or ethoxy-substituted methyl, ethyl, n- or i-propyl.

$R^2$ particularly preferably represents carboxyl, cyano, carbamoyl, thiocarbamoyl or represents in each case optionally cyano-, fluorine-, chlorine-, methoxy- or ethoxy-substituted methyl, ethyl, n- or i-propyl, methoxycarbonyl, ethoxy-carbonyl, n- or i-propoxycarbonyl.

$R^3$ particularly preferably represents hydrogen, fluorine, chlorine, bromine, or represents in each case optionally cyano-, fluorine-, chlorine-, methoxy- or ethoxy-substituted methyl, ethyl, n- or i-propyl.

$R^4$ particularly preferably represents hydrogen, fluorine or chlorine.

$R^5$ particularly preferably represents cyano, carbamoyl, thiocarbamoyl, fluorine, chlorine, bromine, or represents in each case optionally fluorine- and/or chlorine-substituted methyl, ethyl, n- or i-propyl, methoxy, ethoxy, n- or i-propoxy.

X particularly preferably represents hydroxyl, mercapto, amino, nitro, formyl, cyano, carboxyl, carbamoyl, thiocarbamoyl, fluorine, chlorine, bromine, sulphonyl, chlorosulphonyl, represents in each case optionally cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propyl-thio-, methylsulphinyl-, ethylsulphinyl-, n- or i-propylsulphinyl-, methylsulphonyl-, ethylsulphonyl-, n- or i-propylsulphonyl-, acetyl-, propionyl-, n- or i-butyroyl-, methoxycarbonyl-, ethoxycarbonyl-, n- or i-propoxycarbonyl-, n-, i-, s- or t-butoxycarbonyl-, propenyloxycarbonyl-, butenyloxycarbonyl-, propinyloxycarbonyl-, butinyloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, represents dimethylamino, diethylamino, acetyl, propionyl, n- or i-butyroyl, methoxy- carbonyl, ethoxycarbonyl, n- or i-propoxycarbonyl, methylaminocarbonyl, ethylaminocarbonyl, n- oder i-propylaminocarbonyl, dimethylaminocarbonyl, diethylaminocarbonyl, acetyloxy, propinoyloxy, n- or i-butyroyloxy, methoxycarbonyloxy, ethoxycarbonyloxy, n- or i-propoxycarbonyloxy, n-, i-, s- or t-butoxycarbonyloxy, methylaminocarbonyloxy, ethylaminocarbonyl-oxy, n- or i-propyl-aminocarbonyloxy, n-, i-, s- or t-butyl-aminocarbonyloxy, dimethylaminocarbonyloxy, diethylaminocarbonyloxy, acetylamino, propionylamino, n- or i-butyroylamino, methoxycarbonylamino, ethoxy-carbonylamino, n- or i-propoxycarbonylamino, methylsulphonylamino, ethyl-sulphonylamino, n- or i-propylsulphonylamino, or represents in each case optionally cyano-, carboxyl-, carbamoyl-, fluorine-, chlorine-, bromine-, methoxycarbonyl-, ethoxycarbonyl-, n- or i-propoxycarbonyl-, methylamino-carbonyl-, ethylaminocarbonyl-, n- or i-propylaminocarbonyl-, dimethylaminocarbonyl- or diethylaminocarbonyl-substituted ethenyl, propenyl, butenyl, propenyloxy, butenyloxy, propenyloxycarbonyl, butenyloxycarbonyl, ethenecarbonyloxy, propenecarbonyloxy, butenecarbonyloxy, ethinyl, propinyl, butinyl, propinyloxy, butinyloxy, propinyloxycarbonyl, butinyloxycarbonyl, ethinecarbonyloxy, propinecarbonyloxy or butinecarbonyloxy, or represents benzoyloxy.

Y particularly preferably represents hydroxyl, mercapto, amino, nitro, formyl, cyano, carboxyl, carbamoyl, thiocarbamoyl, fluorine, chlorine, bromine, sulphonyl, chlorosulphonyl, represents in each case optionally cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propyl-thio-, methylsulphinyl-, ethylsulphinyl-, n- or i-propylsulphinyl-, methylsulphonyl-, ethylsulphonyl-, n- or i-propylsulphonyl-, acetyl-, propionyl-, n- or i-butyroyl-, methoxycarbonyl-, ethoxycarbonyl-, n- or i-propoxycarbonyl-, n-, i-, s- or t-butoxycarbonyl-, propenyloxycarbonyl-, butenyloxycarbonyl-, propinyloxycarbonyl-, butinyloxycarbonyl-, aminocarbonyl-, methylaminocarbonyl-, ethylaminocarbonyl-, n- or i-propylaminocarbonyl-, dimethylaminocarbonyl-, diethylaminocarbonyl-, phenylaminocarbonyl- or benzylaminocarbonyl-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, represents dimethylamino, diethylamino, acetyl, propionyl, n- or i-butyroyl, methylcarbonyloxy, methoxycarbonyl, ethoxycarbonyl, n- or i-propoxycarbonyl, methylaminocarbonyl, ethylaminocarbonyl, n- or i-propylaminocarbonyl, dimethylaminocarbonyl, diethylaminocarbonyl, acetyloxy, propinoyloxy, n- or i-butyroyloxy, methylcarbonyloxy, methoxycarbonyloxy, ethoxycarbonyloxy, n- or i-propoxycarbonyloxy, n-, i-, s- or t-butoxycarbonyloxy, methylaminocarbonyloxy, ethylaminocarbonyloxy, n- or i-propylaminocarbonyloxy, n-, i-, s- or t-butylaminocarbonyloxy, dimethylaminocarbonyloxy, diethylamino-carbonyloxy, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, or represents in each case optionally cyano-, carboxyl-, carbamoyl-, fluorine-, chlorine-, bromine-, methoxycarbonyl-, ethoxycarbonyl-, n- or i-propoxycarbonyl-, methylaminocarbonyl-, ethylaminocarbonyl-, n- or i-propylamino-carbonyl-, dimethylaminocarbonyl- or diethylaminocarbonyl-substituted ethenyl, propenyl, butenyl, propenyloxy, butenyloxy, propenyloxycarbonyl, butenyloxycarbonyl, ethenecarbonyloxy, propenecarbonyloxy, butenecarbonyloxy, ethinyl, propinyl, butinyl, propinyloxy, butinyloxy, propinyloxycarbonyl, butinyloxycarbonyl, ethinecarbonyloxy, propinecarbonyloxy or butinecarbonyloxy, or represents benzoyloxy.

m very particularly preferably represents 0.

n very particularly preferably represents 0 or 1.

Q very particularly preferably represents O (oxygen).

$R^1$ very particularly preferably represents hydrogen, amino or methyl.

$R^2$ very particularly preferably represents carboxyl, cyano, carbamoyl, thio-carbamoyl or represents in each case optionally fluorine- and/or chlorine-substituted methyl, ethyl, methoxycarbonyl or ethoxycarbonyl.

$R^3$ very particularly preferably represents hydrogen, fluorine, chlorine, bromine, or represents optionally fluorine- and/or chlorine-substituted methyl.

$R^4$ very particularly preferably represents fluorine.

$R^5$ very particularly preferably represents cyano, carbamoyl, thiocarbamoyl, fluorine, chlorine, bromine, or represents in each case optionally fluorine-and/or chlorine-substituted methyl or methoxy.

X very particularly preferably represents hydroxyl, mercapto, amino, nitro, formyl, cyano, carboxyl, carbamoyl, thiocarbamoyl, fluorine, chlorine, bromine, sulphonyl, chlorosulphonyl, represents in each case optionally cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, propenyloxycarbonyl-, methylaminocarbonyl-, ethylaminocarbonyl-, n- or i-propylaminocarbonyl-, di-methylaminocarbonyl- or benzyloxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethyl-sulphonyl, methylamino, ethylamino, n- or i-propylamino, represents dimethylamino, diethylamino, acetyl, propionyl, n- or i-butyroyl, methoxy-carbonyl, ethoxycarbonyl, n- or i-propoxycarbonyl, methylaminocarbonyl, ethylaminocarbonyl, n- oder i-propylaminocarbonyl, dimethylaminocarbonyl, diethylaminocarbonyl, acetyloxy, propinoyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, dimethylaminocarbonyloxy, diethylaminocarbonyloxy, acetyl-amino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, or represents in each case optionally cyano-, carboxyl-, carbamoyl-, fluorine-, chlorine-, bromine-, methoxycarbonyl-, ethoxycarbonyl-, n- or i-propoxycarbonyl-, methylamino-carbonyl-, ethylaminocarbonyl-, n- or i-propylaminocarbonyl-, dimethyl-aminocarbonyl- or diethylarninocarbonyl-substituted ethenyl, propenyl, butenyl, propenyloxy, butenyloxy, propenyloxycarbonyl, butenyloxycarbonyl, ethinyl, propinyl, butinyl, propinyloxy, butinyloxy, propenyloxy-carbonyl or butinyloxycarbonyl, or represents benzoyloxy.

Y very particularly preferably represents hydroxyl, mercapto, amino, nitro, formyl, cyano, carboxyl, carbamoyl, thiocarbamoyl, fluorine, chlorine, bromine, sulpho, chlorosulphonyl, represents in each case optionally cyano-, carboxyl-, carbamoyl-, thiocarbamoyl-, fluorine-, chlorine-, bromine-, methoxy-, ethoxy-,.n- or i-propoxy-, methylthio-, ethylthio-, n- or i-propyl-thio-, methylsulphinyl-, ethylsulphinyl-, methylsulphonyl-, ethylsulfonyl-, acetyl-, propionyl-, n- or i-butyroyl-, methoxycarbonyl-, ethoxycarbonyl-, n- or i-propoxycarbonyl-, propenyloxycarbonyl-, aminocarbonyl-, methylamino-carbonyl-, ethylaminocarbonyl-, n- or i-propylaminocarbonyl-, dimethyl-aminocarbonyl-, phenylaminocarbonyl- or benzyloxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methyl-sulphonyl, ethylsulphonyl, methylamino, ethylamino, n- oder i-propylamino, represents dimethylamino, diethylamino, acetyl, propionyl, n- or i-butyroyl, methoxycarbonyl, ethoxycarbonyl, n- or i-propoxycarbonyl, methylamino-carbonyl, ethylaminocarbonyl, n- or i-propylaminocarbonyl, dimethylamino- carbonyl, diethylaminocarbonyl, acetyloxy, propinoyloxy, n- or i-butyroyl-oxy, methylcarbonyloxy, methoxycarbonyloxy, ethoxycarbonyloxy, n- or i-propoxycarbonyloxy, methylaminocarbonyloxy, ethylaminocarbonyloxy, n- or i-propyl-aminocarbonyloxy, dimethylaminocarbonyloxy, diethylamino-carbonyloxy, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, or represents in each case optionally cyano-, carboxyl-, carbamoyl-, fluorine-, chlorine-, bromine-, methoxycarbonyl-, ethoxycarbonyl-, n- or i-propoxy-carbonyl-, methylaminocarbonyl-, ethyl-aminocarbonyl-, n- or i-propylamino-carbonyl-, dimethylaminocarbonyl- or diethylaminocarbonyl-substituted ethenyl, propenyl, butenyl, propenyloxy, butenyloxy, propenyloxycarbonyl, butenyl-oxycarbonyl, ethinyl, propinyl, butinyl, propinyloxy, butinyloxy, propinyloxycarbonyl or butinyloxycarbonyl, or represents benzoyloxy.

$R^2$ most preferably represents trifluoromethyl.

$R^3$ most preferably represents hydrogen.

$R^5$ most preferably represents cyano.

Y most preferably represents hydroxyl, methoxy, represents in each case meth-oxycarbonyl-, ethoxycarbonyl-, methylaminocarbonyl-, dimethylaminocarb-onyl or phenylaminocarbonyl-substituted methoxy or ethoxy, represents methylaminocarbonyloxy, methylcarbonyloxy, propinyloxy, butinyloxy or ethoxycarbonyloxy.

A very particularly preferred group is the compounds of the general formula (IA)

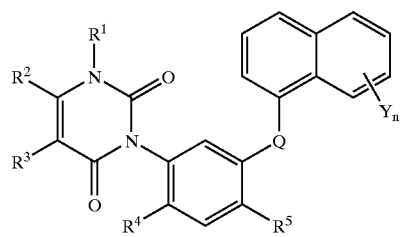

(IA)

in which n, Q, $R^1$, $R^2$, $R^3$, $R^4$, $R^5$ and Y each have the meanings given above as being very particularly preferred or most preferred.

A further very particularly preferred group is the compounds of the general formula (IB)

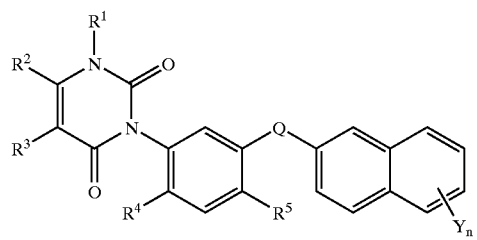

(IB)

in which n, Q, $R^1$, $R^2$, $R^3$, $R^4$, $R^5$ and Y each have the meanings given above as being very particularly preferred or as being most preferred.

The abovementioned or preferred radical definitions apply both to the end products of the formula (I) and correspondingly to the starting materials or intermediates required in each case for the preparation. These radical definitions can be combined with one another at will, i.e. including combinations between the given preferred ranges.

Preference according to the invention is given to those compounds of the formula (I) which contain a combination of the meanings listed above as being preferred ("preferably").

Particular preference according to the invention is given to those compounds of the formula (I) which contain a combination of the meanings given above as being particularly preferred.

Very particular preference according to the invention is given to those compounds of the formula (I) which contain a combination of the meanings given above as being very particularly preferred.

Most preference according to the invention is given to those compounds of the formula (I) which contain a combination of the meanings given above as being most preferred.

Saturated or unsaturated hydrocarbon radicals, such as alkyl or alkenyl, are—including in combination with heteroatoms, such as in alkoxy—in each case straight-chain or branched as far as this is possible.

Optionally substituted radicals can be mono- or polysubstituted, where in the case of polysubstitution the substituents can be identical or different.

If the compounds of the general formula (I) according to the invention contain substituents with asymmetric carbon atoms, the invention relates in each case to the R enantiomers and the S enantiomers and to any mixures of these enantiomers, in particular the racemates. In the case of compounds of the formula (I) having alkenyl substituents, the invention relates in each case to the possible E and Z isomers and their mixtures.

Examples of the compounds of the general formula (I) according to the invention are listed in the groups below.

Group 1

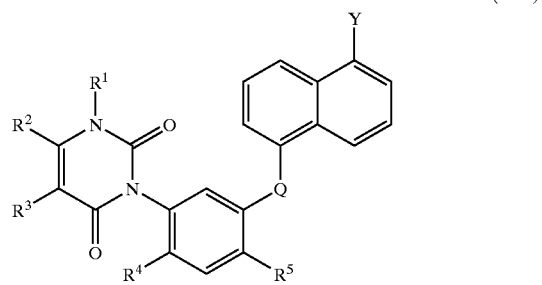

(IA-1)

Here, Q, $R^1$, $R^2$, $R^3$, $R^4$, $R^5$ and Y each have the meanings given below in tabular form.

| Q | $R^1$ | $R^2$ | $R^3$ | $R^4$ | $R^5$ | Y |
|---|---|---|---|---|---|---|
| O | H | $CF_3$ | H | F | CN | — |
| O | $CH_3$ | $CF_3$ | H | F | CN | — |
| S | H | $CF_3$ | H | F | CN | — |
| S | $CH_3$ | $CF_3$ | H | F | CN | — |
| O | H | $CF_3$ | Cl | F | CN | — |
| O | $CH_3$ | $CF_3$ | Cl | F | CN | — |
| O | H | $CF_3$ | $CH_3$ | F | CN | — |

-continued

| Q | R¹ | R² | R³ | R⁴ | R⁵ | Y |
|---|---|---|---|---|---|---|
| O | CH₃ | CF₃ | CH₃ | F | CN | — |
| O | H | CF₃ | H | F | CN | OH |
| O | CH₃ | CF₃ | H | F | CN | OH |
| O | H | CF₃ | H | F | CN | OCH₃ |
| O | CH₃ | CF₃ | H | F | CN | OCH₃ |
| O | H | CN | H | F | CN | OCH₃ |
| O | CH₃ | CN | H | F | CN | OCH₃ |
| O | H | CF₃ | H | F | Cl | OCH₃ |
| O | CH₃ | CF₃ | H | F | Cl | OCH₃ |
| O | H | CF₃ | H | F | CN |  |
| O | CH₃ | CF₃ | H | F | CN | 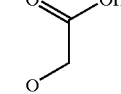 |
| O | H | CF₃ | H | F | CN | 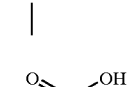 |
| O | CH₃ | CF₃ | H | F | CN | 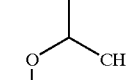 |
| O | H | CF₃ | H | F | CN | 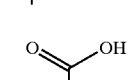 |
| O | CH₃ | CF₃ | H | F | CN | 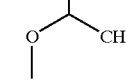 |
| O | H | CF₃ | H | F | CN | 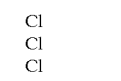 |
| O | CH₃ | CF₃ | H | F | CN | 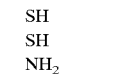 |

-continued

| Q | R¹ | R² | R³ | R⁴ | R⁵ | Y |
|---|---|---|---|---|---|---|
| O | H | CF₃ | H | F | CN | 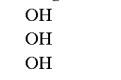 |
| O | CH₃ | CF₃ | H | F | CN | 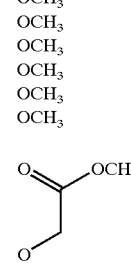 |
| O | H | CF₃ | H | F | CN | 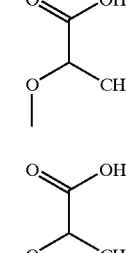 |
| O | CH₃ | CF₃ | H | F | CN | 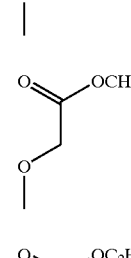 |
| O | H | CF₃ | H | F | CN | Cl |
| O | CH₃ | CF₃ | H | F | CN | Cl |
| S | H | CF₃ | H | F | CN | Cl |
| S | CH₃ | CF₃ | H | F | CN | Cl |
| O | H | CF₃ | H | F | CN | SH |
| O | CH₃ | CF₃ | H | F | CN | SH |
| O | H | CF₃ | H | F | CN | NH₂ |
| O | CH₃ | CF₃ | H | F | CN | NH₂ |
| O | H | CF₃ | H | Cl | Cl | OH |
| O | CH₃ | CF₃ | H | Cl | Cl | OH |
| O | H | CF₃ | H | H | CN | OH |
| O | CH₃ | CF₃ | H | H | CN | OH |
| O | H | CF₃ | H | F | CN | 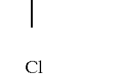 |
| O | CH₃ | CF₃ | H | F | CN | 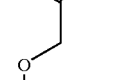 |
| O | H | CF₃ | H | F | CN | SCH₃ |
| O | CH₃ | CF₃ | H | F | CN | SCH₃ |
| O | H | CF₃ | H | F | CN | SO₃H |
| O | CH₃ | CF₃ | H | F | CN | SO₃H |
| O | H | CF₃ | H | F | CN | SO₃Na |
| O | CH₃ | CF₃ | H | F | CN | SO₃Na |
| O | H | CF₃ | H | F | CN | 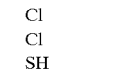 |

-continued

| Q | R¹ | R² | R³ | R⁴ | R⁵ | Y |
|---|----|----|----|----|----|---|
| O | CH₃ | CF₃ | H | F | CN | 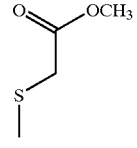 |
| O | H | CF₃ | H | F | CN | 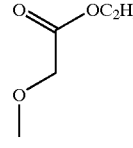 |
| O | CH₃ | CF₃ | H | F | CN | 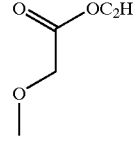 |
| O | H | CF₃ | H | F | CN | 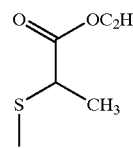 |
| O | CH₃ | CF₃ | H | F | CN | 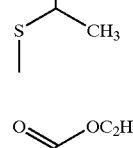 |
| O | H | CF₃ | H | F | CN | 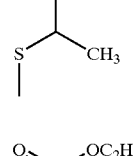 |
| O | CH₃ | CF₃ | H | F | CN | 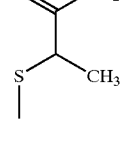 |
| O | H | CF₃ | H | F | CN | 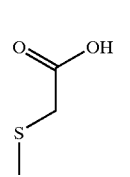 |
| O | CH₃ | CF₃ | H | F | CN |  |

-continued

| Q | R¹ | R² | R³ | R⁴ | R⁵ | Y |
|---|----|----|----|----|----|---|
| O | H | CF₃ | H | F | CN | 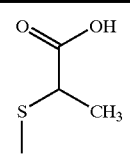 |
| O | CH₃ | CF₃ | H | F | CN | 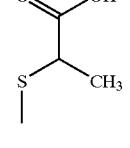 |
| O | H | CF₃ | H | F | CN | 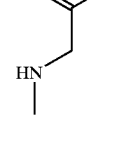 |
| O | CH₃ | CF₃ | H | F | CN | 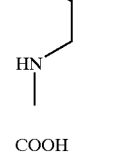 |
| O | H | CF₃ | H | F | CN | COOH |
| O | CH₃ | CF₃ | H | F | CN | COOH |
| O | H | CF₃ | H | F | CN | COOCH₃ |
| O | CH₃ | CF₃ | H | F | CN | COOCH₃ |
| O | H | CF₃ | H | F | CN | COOC₂H₅ |
| O | CH₃ | CF₃ | H | F | CN | COOC₂H₅ |
| O | H | CF₃ | H | F | CN | CH₃ |
| O | CH₃ | CF₃ | H | F | CN | CH₃ |
| O | H | CF₃ | H | F | CN | CH₂Cl |
| O | CH₃ | CF₃ | H | F | CN | CH₂Cl |
| O | H | CF₃ | H | F | CN | CH₂Br |
| O | CH₃ | CF₃ | H | F | CN | CH₂Br |
| O | H | CF₃ | H | F | CN | 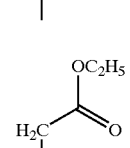 |
| O | CH₃ | CF₃ | H | F | CN | 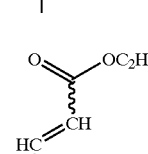 |
| O | H | CF₃ | H | F | CN | 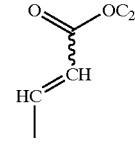 |
| O | CH₃ | CF₃ | H | F | CN |  |

-continued
| Q | R¹ | R² | R³ | R⁴ | R⁵ | Y |
|---|----|----|----|----|----|---|
| O | H | CF₃ | H | F | CN | 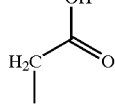 |
| O | CH₃ | CF₃ | H | F | CN | 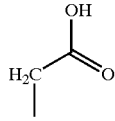 |
| O | H | CF₃ | H | F | CN | 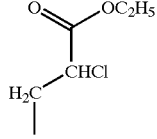 |
| O | CH₃ | CF₃ | H | F | CN | 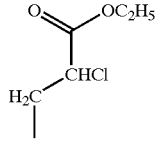 |
| O | H | CF₃ | H | F | CN | COOC₃H₇-i |
| O | CH₃ | CF₃ | H | F | CN | COOC₃H₇-i |
| O | H | CF₃ | H | F | CN | 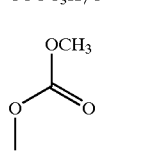 |
| O | CH₃ | CF₃ | H | F | CN | 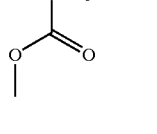 |
| O | H | CF₃ | H | F | CN | 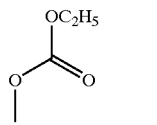 |
| O | CH₃ | CF₃ | H | F | CN | 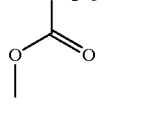 |
| O | H | CF₃ | H | F | CN | 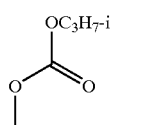 |
| O | CH₃ | CF₃ | H | F | CN | 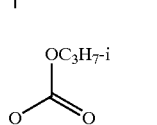 |
-continued
| Q | R¹ | R² | R³ | R⁴ | R⁵ | Y |
|---|----|----|----|----|----|---|
| O | H | CF₃ | H | F | Cl | 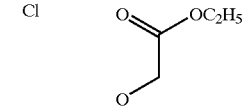 |
| O | CH₃ | CF₃ | H | F | Cl | 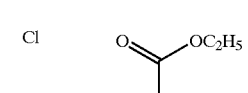 |
| O | H | CF₃ | H | F | Br | 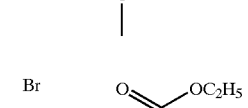 |
| O | CH₃ | CF₃ | H | F | Br | 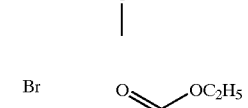 |
| O | CH₃ | CF₃ | H | F |  | 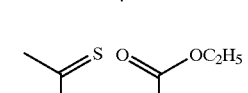 |
| O | CH₃ | CF₃ | H | F |  | 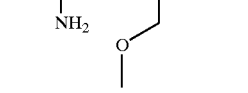 |
| O | CH₃ | CF₃ | H | F |  | 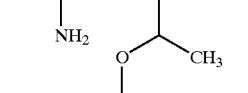 |
| O | CH₃ | CF₃ | H | F |  | 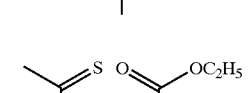 |
| O | CH₃ | CN | H | F | CN | 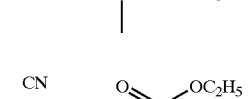 |

-continued
| Q | R¹ | R² | R³ | R⁴ | R⁵ | Y |
|---|----|----|----|----|----|---|
| O | CH₃ | CN | H | F | CN | 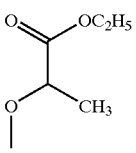 |
| O | CH₃ | CF₃ | H | Cl | Cl | 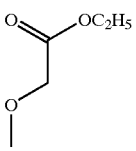 |
| O | CH₃ | CF₃ | H | Cl | Cl | 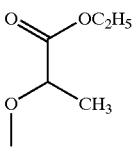 |
| O | NH₂ | CF₃ | H | F | CN | 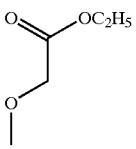 |
| O | NH₂ | CF₃ | H | F | CN | 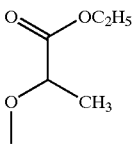 |
| O | CH₃ | CHF₂ | H | F | CN | OH |
| O | CH₃ | CHF₂ | H | F | CN | 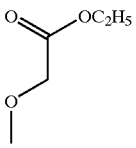 |
| O | CH₃ | CF₂Cl | H | F | CN | OH |
| O | CH₃ | CF₂Cl | H | F | CN | 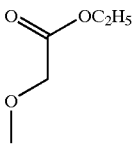 |
| O | CH₃ | C₂F₅ | H | F | CN | OH |
| O | CH₃ | C₂F₅ | H | F | CN | 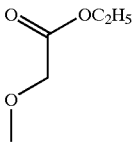 |
| O | CH₃ | CF₃ | H | F | CN | 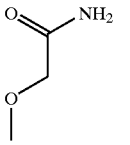 |
| O | CH₃ | CF₃ | H | F | CN | CHO |
| O | CH₃ | CF₃ | H | F | CN | 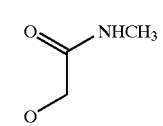 |
| O | CH₃ | CF₃ | H | F | CN | 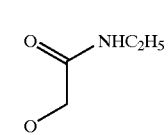 |
| O | CH₃ | CF₃ | H | F | CN | 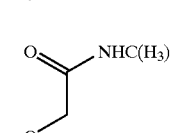 |
| O | CH₃ | CF₃ | H | F | CN | 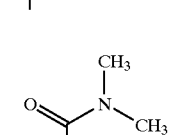 |
| O | CH₃ | CF₃ | H | F | CN | 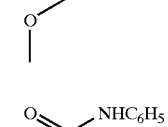 |
| O | CH₃ | CF₃ | H | F | CN | 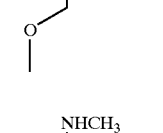 |
| O | CH₃ | CF₃ | H | F | CN | 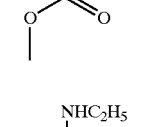 |
| O | CH₃ | CF₃ | H | F | CN | 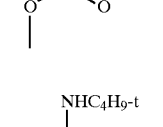 |
| O | CH₃ | CF₃ | H | F | CN | 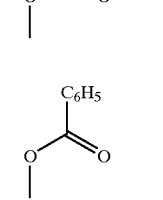 |

-continued

| Q | R¹ | R² | R³ | R⁴ | R⁵ | Y |
|---|----|----|----|----|----|---|
| O | CH₃ | CF₃ | H | F | CN |  |
| O | CH₃ | CF₃ | H | F | CN | 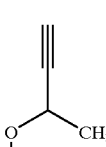 |
| O | CH₃ | CF₃ | Cl | F | CN | 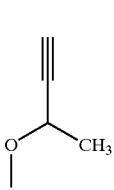 |

Group 2

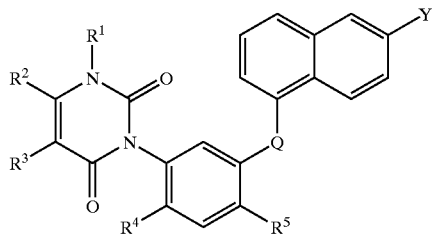
(IA-2)

Here, Q, R¹, R², R³, R⁴, R⁵ and Y each have the meanings given above in group 1 in tabular form.

Group 3

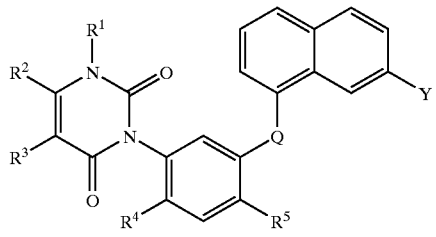
(IA-3)

Here, Q, R¹, R², R³, R⁴, R⁵ and Y each have the meanings given above in group 1 in tabular form.

Group 4

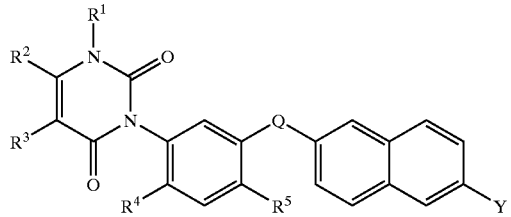
(IB-1)

Here, Q, R¹, R², R³, R⁴, R⁵ and Y each have the meanings given above in group 1 in tabular form.

Group 5

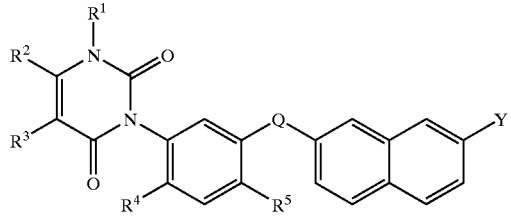
(IB-2)

Here, Q, R¹, R², R³, R⁴, R⁵ and Y each have the meanings given above in group 1 in tabular form.

Group 6

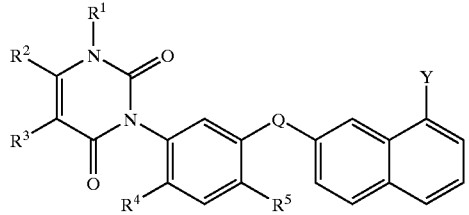
(IB-3)

Here, Q, R¹, R², R³, R⁴, R⁵ and Y each have the meanings given above in group 1 in tabular form.

Group 7

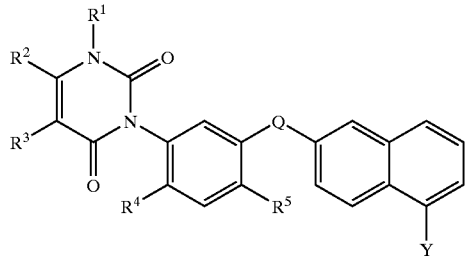
(IB-4)

Here, Q, R¹, R², R³, R⁴, R⁵ and Y each have the meanings given above in group 1 in tabular form.

Group 8

(IA-4)

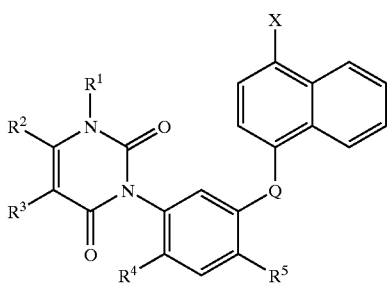

Here, Q, $R^1$, $R^2$, $R^3$, $R^4$ and $R^5$ have the meanings given above in Group 1 in tabular form; X has the meanings given above in Group 1 for Y.

The novel substituted phenyluracils of the general formula (I) have interesting biological properties. In particular, they have strong herbicidal activity.

The novel substituted phenyluracils of the general formula (I) are obtained when (a) halogenophenyluracils of the general formula (II)

(II)

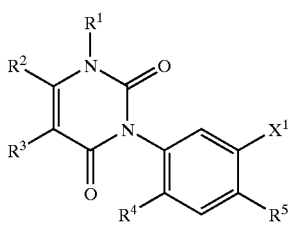

in which
$R^1$, $R^2$, $R^3$, $R^4$ and $R^5$ are each as defined above and
$X^1$ represents halogen,
are reacted with naphthalene derivatives of the general formula (III)

(III)

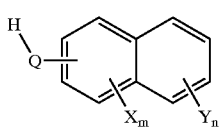

in which
m, n, Q, X und Y are each as defined above,
or with alkali metal salts of compounds of the formula (III)
if appropriate in the presence of a reaction auxiliary and if appropriate in the presence of a diluent,
or when (b) aminoalkenoic acid esters of the general formula (IV)

(IV)

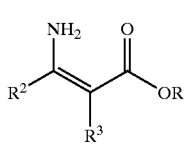

in which
$R^2$ and $R^3$ are each as defined above and
R represents alkyl, aryl or arylalkyl,
are reacted with aryl isocyanates of the general formula (V)

(V)

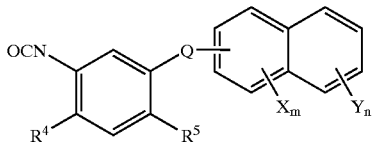

in which
m, n, Q, $R^4$, $R^5$, X and Y are as defined above,
or with arylurethanes (arylcarbamates) of the general formula (VI)

(VI)

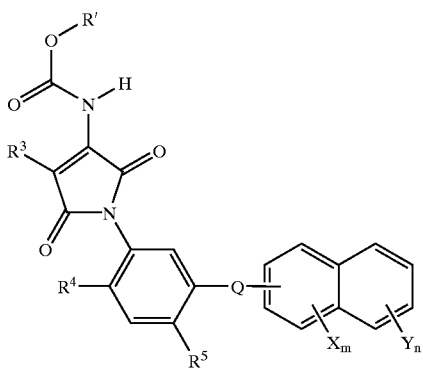

in which
m, n, Q, $R^4$, $R^5$, X and Y are as defined above and
R represents alkyl, aryl or arylalkyl, if appropriate in the presence of a reaction auxiliary and if appropriate in the presence of a diluent, or when (c) N-aryl-1-alkoxycarbonylamino-maleimides of the general formula (VII)

(VII)

in which
m, n, Q, $R^3$, $R^4$, $R^5$, X and Y are as defined above and
R represents alkyl, are reacted with a metal hydride in the presence of water and, if appropriate, in the presence of an organic solvent, or when (d) substituted phenyluracils of the general formula (Ia)

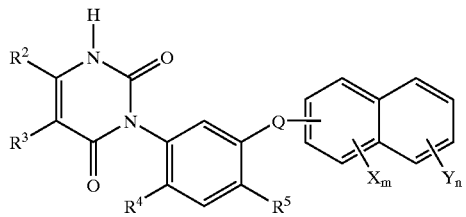
(Ia)

in which m, n, Q, $R^2$, $R^3$, $R^4$, $R^5$, X and Y are as defined above, are reacted with 1-aminooxy-2,4-dinitro-benzene or with alkylating agents of the general formula (VIII)

$X^2-A^1$ (VIII)

in which $A^1$ represents optionally substituted alkyl and $X^2$ represents halogen or the grouping —O—SO$_2$—O—$A^1$, if appropriate in the presence of a reaction auxiliary and if appropriate in the presence of a diluent, and electrophilic or nucleophilic and/or oxidation or reduction reactions within the scope of the definition of the substituents are, if appropriate, subsequently carried out in a customary manner.

The compounds of the general formula (I) can be converted by customary methods into other compounds of the general formula (I) according to the above definition, for example by etherification or ether cleavage (X,Y: OH→OC$_2$H$_5$, OCH$_3$→OH), esterification or hydrolysis (for example X: OCH$_2$COOH→OCH$_2$COOC$_2$H$_5$, OCH(CH$_3$)COOCH$_3$→OCH(CH$_3$)COOH), reaction with dicyano or hydrogen sulphide (for example $R^5$: Br→CN, CN→CSNH$_2$), conversion of carboxyl compounds into other carboxylic acid derivatives by customary methods (for example $R^2$: COOH→CN, COOH→COOCH$_3$), conversion of sulfonic acid derivatives according to customary methods (for example X,Y: SO$_3$Na→SO$_2$Cl, SO$_2$Cl→SH), halogenation (for example X,Y: CH$_3$→CH$_2$Cl or CH$_2$Br)—cf. the Preparation Examples.

Using, for example, 1-(4-cyano-2,5-difluoro-phenyl)-4-chlorodifluoromethyl-3,6-dihydro-2,6-dioxo- 1(2H)-pyrimidine and 5-methoxy-1-naphthol as starting materials, the course of the reaction of process (a) according to the invention can be illustrated by the following formula scheme:

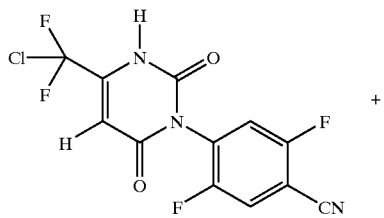

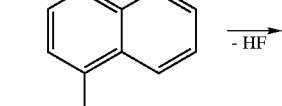

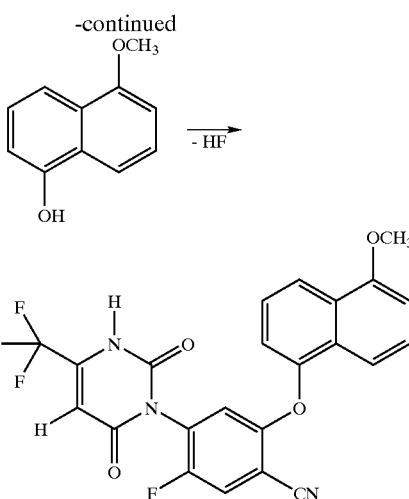

Using, for example, methyl 3-amino-4,4,4-trifluorocrotonate and 4-cyano-2-fluoro-5-(2-naphthyloxy)-phenyl isocyanate as starting materials, the course of the reaction in the process (b) according to the invention can be illustrated by the following scheme:

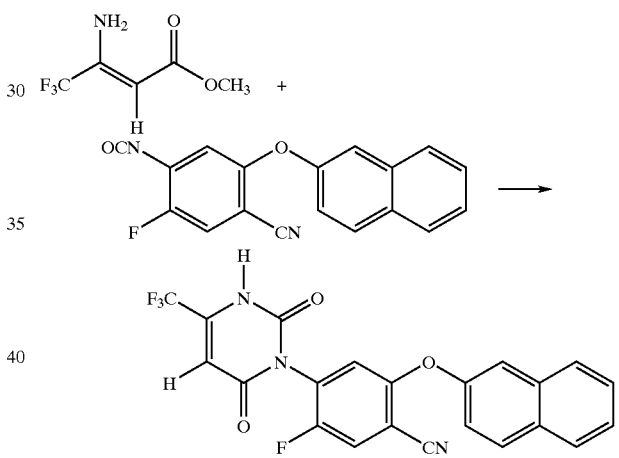

Using, for example, methyl [1-(2,4-dichloro-5-(1-naphthylthio)-phenyl)-2,5-dioxo-2,5-dihydro-1H-pyrrol-3-yl]-carbamate as starting material, the course of the reaction in the process (c) according to the invention can be illustrated by the following formula scheme:

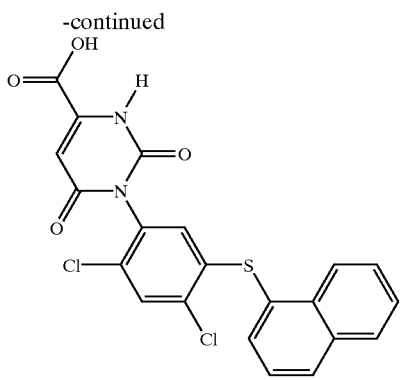

Using, for example, 1-[2-chloro-4-trifluoromethyl-5-(6-methoxycarbonylmethoxy-2-naphthyloxy)-phenyl]-4-difluoromethyl-3,6-dihydro-2,6-dioxo-1(2H)-pyrimidine and methyl bromide as starting materials, the course of the reaction in the process (d) according to the invention can be illustrated by the following formula scheme:

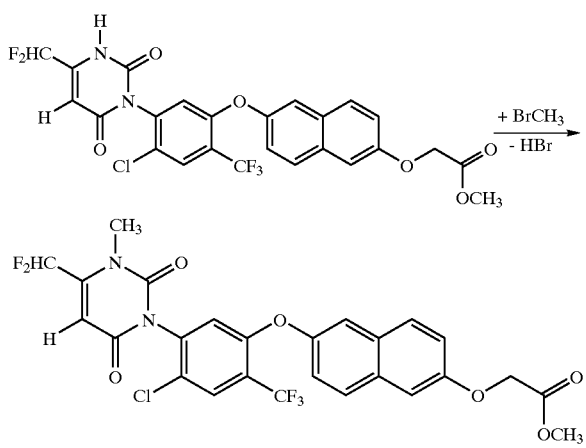

The formula (II) provides a general definition of the halogenophenyluracils to be used as starting materials in the process (a) according to the invention for preparing compounds of the formula (I). In the formula (II), $R^1$, $R^2$, $R^3$, $R^4$ and $R^5$ each preferably have those meanings which have already been mentioned above, in connection with the description of the compounds of the formula (I) according to the invention, as being preferred, particularly preferred, very particularly preferred or most preferred for $R^1$, $R^2$, $R^3$, $R^4$ and $R^5$; $X^1$ preferably represents fluorine or chlorine, in particular fluorine.

The starting materials of the general formula (II) are known and/or can be prepared by processes known per se (cf. EP-A-648749).

The formula (III) provides a general definition of the naphthalene derivatives further to be used as starting materials in the process (a) according to the invention. In the formula (III), m, n, Q, X and Y each preferably have those meanings which have already been mentioned above, in connection with the description of the compounds of the formula (I) according to the invention, as being preferred, particularly preferred, very particularly preferred or most preferred for m, n, Q, X and Y.

The starting materials of the general formula (III) are known organic chemicals for synthesis.

The formula (IV) provides a general definition of the aminoalkenoic acid esters to be used as starting materials in the process (b) according to the invention for preparing compounds of the general formula (I). In the general formula (IV), $R^2$ and $R^3$ each preferably have those meanings which have already been mentioned above, in connection with the description of the compounds of the general formula (I) according to the invention, as being preferred, particularly preferred, very particularly preferred or most preferred for $R^2$ and $R^3$; R preferably represents $C_1$–$C_4$-alkyl, phenyl or benzyl, in particular methyl or ethyl.

The starting materials of the general formula (IV) are known and/or can be prepared by processes known per se (cf. J. Heterocycl. Chem. 9 (1972), 513–522).

Formula (V) provides a general definition of the aryl isocyanates further to be used as starting materials in the process (b) according to the invention. In the general formula (V), m, n, Q, $R^4$, $R^5$, X and Y each preferably have those meanings which have already been mentioned above, in connection with the description of the compounds of the general formula (I) according to the invention, as being preferred, particularly preferred, very particularly preferred or most preferred for m, n, Q, $R^4$, $R^5$, X and Y.

The starting materials of the general formula (V) have hitherto not been disclosed in the literature; as novel compounds, they also form part of the subject-matter of the present application.

The novel aryl isocyanates of the general formula (V) are obtained by reacting aniline derivatives of the general formula (IX)

(IX)

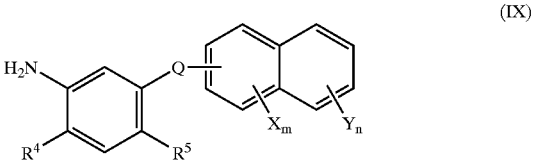

in which m, n, Q, $R^4$, $R^5$, X and Y are each as defined above with phosgene in the presence of a diluent, such as, for example, chlorobenzene, at temperatures between −20° C. and +150° C. (cf., for example, also EP-A-648749).

The formula (VI) provides a general definition of the arylurethanes to be used, if appropriate, as starting materials in the process (b) according to the invention. In the general formula (VI), m, n, Q, $R^4$, $R^5$, X and Y each preferably have those meanings which have already been mentioned above, in connection with the description of the compounds of the general formula (I) according to the invention, as being preferred, particularly preferred, very particularly preferred or most preferred for m, n, Q, $R^4$, $R^5$, X and Y; R preferably represents $C_1$–$C_4$-alkyl, phenyl or benzyl, in particular methyl or ethyl.

The starting materials of the general formula (VI) have hitherto not been disclosed in the literature; as novel compounds, they also form part of the subject-matter of the present application.

The novel arylurethanes of the general formula (VI) are obtained by reacting aniline derivatives of the general formula (IX)

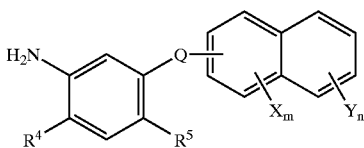 (IX)

in which
m, n, Q, $R^4$, $R^5$, X and Y are each as defined above,
with chlorocarbonyl compounds of the general formula (X)

<p style="text-align:center">RO—CO—Cl     (X)</p> in which
R is as defined above,
if appropriate in the presence of an acid acceptor, such as, for example, pyridine, and if appropriate in the presence of a diluent, such as, for example, methylene chloride, at temperatures between −20° C. and +100° C. (cf. the Preparation Examples).

The aniline derivatives of the general formula (IX) required as precursors have hitherto not been disclosed in the literature; as novel compounds, they also form part of the subject-matter of the present application.

The novel aniline derivatives of the general formula (IX) are obtained by reacting anilines of the general formula (XI)

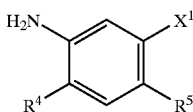 (XI)

in which
$R^4$, $R^5$ and $X^1$ are each as defined above,
with naphthalene derivatives of the general formula (III)

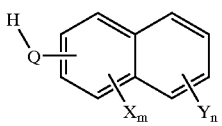 (III)

in which
m, n, Q, X and Y are each as defined above,
or with alkali metal salts of compounds of the formula (III)
if appropriate in the presence of a reaction auxiliary, such as, for example, sodium hydride, and if appropriate in the presence of a diluent, such as, for example, N-methyl-pyrrolidone, at temperatures between 0° C. and 150° C. (cf. the Preparation Examples).

The formula (VII) provides a general definition of the N-aryl-1-alkoxycarbonylamino-maleimides to be used as starting materials in the process (c) according to the invention for preparing compounds of the general formula (I). In the general formula (VII), m, n, Q, $R^3$, $R^4$, $R^5$, X and Y each preferably have those meanings which have already been mentioned above, in connection with the description of the compounds of the general formula (I) according to the invention, as being preferred, particularly preferred, very particulaly preferred or most preferred form, n, Q, $R^3$, $R^4$, $R^5$, X and Y; $R^6$ preferably represents $C_1$–$C_4$-alkyl, in particular methyl or ethyl.

The novel N-aryl-1-alkoxycarbonylamino-maleimides of the general formula (VII) are obtained by reacting alkyl (2,5-dioxo-2,5-dihydro-furan-3-yl)-carbamates of the general formula (XII)

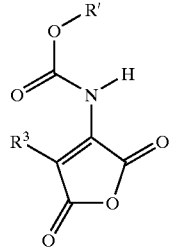 (XII)

in which
$R^3$ is as defined above and
R' represents alkyl, (in particular methyl or ethyl),
with aniline derivatives of the general formula (IX)

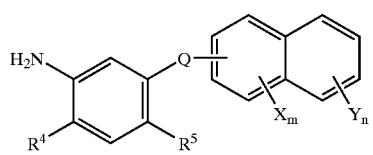 (IX)

in which
m, n, Q, $R^4$, $R^5$, X and Y are each as defined above,
if appropriate in the presence of a diluent, such as, for example, acetic acid, at temperatures between 0° C. and 200° C., preferably between 50° C. and 150° C.

The precursors of the general formula (XII) are known and/or can be prepared by processes known per se (cf. DE 19604229).

The formula (Ia) provides a general definition of the substituted phenyluracils to be used as starting materials in the process (d) according to the invention for preparing compounds of the formula (I). In the formula (Ia), m, n, Q, $R^2$, $R^3$, $R^4$, $R^5$, X and Y each preferably have those meanings which have already been mentioned above, in connection with the description of the compounds of the formula (I) according to the invention, as being preferred, particularly preferred, very particularly preferred or most preferred for m, n, Q, $R^2$, $R^3$, $R^4$, $R^5$, X and Y.

As novel substances, the starting materials of the general formula (Ia) for process (b) also form part of the subject-matter of the present application; they can be prepared according to processes (a), (b) and (c) according to the invention.

The formula (VIII) provides a general definition of the alkylating agents further to be used as starting materials in the process (d) according to the invention. In the formula (VIII), $A^1$ preferably represents optionally cyano-, halogen- or $C_1$–$C_4$-alkoxy-substituted alkyl having 1 to 4 carbon atoms and $X^2$ represents chlorine, bromine, iodine, methylsulphonyloxy or ethylsulphonyloxy; $A^1$ particularly preferably represents in each case optionally cyano-, fluorine-, chlorine-, methoxy- or ethoxy-substituted methyl, ethyl, n- or i-propyl and $X^2$ represents chlorine, bromine, iodine, methylsulphonyloxy or ethylsulphonyloxy.

The starting materials of the formula (VIII) are known organic chemicals for synthesis.

The processes according to the invention for preparing the compounds of the general formula (I) are preferably carried out using diluents. Suitable diluents for carrying out the processes (a), (b), (c) and (d) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a), (b), (c) and (d) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexyl-amine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Other suitable reaction auxiliaries for the processes according to the invention are phase-transfer catalysts. Examples of such catalysts which may be mentioned are:

Tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutyl-phosphonium bromide, tetrabutylphosphonium chloride, tributyl-hexadecyl-phosphonium bromide, butyl-triphenylphosphonium chloride, ethyl-trioctyl-phosphonium bromide, tetraphenylphosphonium bromide.

When carrying out the processes (a), (b), (c) and (d) according to the invention, the reaction temperatures can be varied within a relatively wide range. In general, the processes are carried out at temperatures between 0° C. and 150° C., preferably if between 10° C. and 120° C.

The processes according to the invention are generally carried out under atmospheric pressure. However, it is also possible to carry out the processes according to the invention under elevated or reduced pressure - in general between 0.1 bar and 10 bar.

For carrying out the process according to the invention, the starting materials are generally employed in approximately equimolar amounts. However, it is also possible for one of the components to be used in a relatively large excess. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolwlus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

Depending on the concentration, the active compounds according to the invention are suitable for total weed control, for example on industrial terrain and railway tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The active compounds of the formula (I) according to the invention have strong herbicidal activity and a broad activity spectrum when used on the soil and on above-ground parts of plants. To a certain extent, they are also suitable for the selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropyl-ammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuiron, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

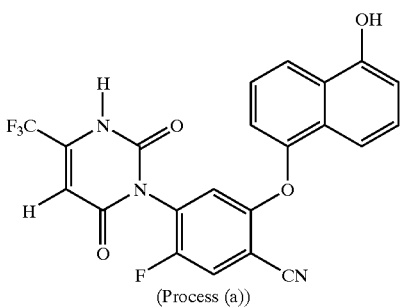

(Process (a))

4.04 g (25 mmol) of 1,5-dihydroxy-naphthalene are initially charged in 100 ml of dimethyl sulphoxide and admixed with 2.5 g (25 mmol) of sodium hydride (60%), and the mixture is stirred for 30 minutes. 8.0 g (25 mmol) of 1-(4-cyano-2,5-difluoro-phenyl)-4-trifluoromethyl-3,6-dihydro-2,6-dioxo-1(2H)-pyrimidine are then added and the reaction mixture is stirred at from 60° C. to 70° C. for 20 hours and then poured into about the same amount of 2N hydrochloric acid. The resulting crystalline product is isolated by filtration with suction and purified by column chromatography (silica gel, chloroform/ethyl acetate, vol. 1:1).

This gives (as second fraction) 2.9 g (25% of theory) of 4-(2,6-dioxo-4-trifluoro-methyl-3,6-dihydro-1(2) pyrimidinyl)-5-fluoro-2-(5-hydroxy-1-naphthyloxy)-benzonitrile of melting point 168° C.

Example 2

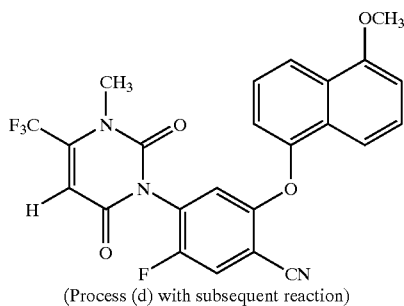

(Process (d) with subsequent reaction)

A mixture of 32.6 g (71 mmol) of 4-(2,6-dioxo-4-trifluoromethyl-3,6-dihydro-1(2H)-pyrimidinyl)-5-fluoro-2-(5-hydroxy-1-naphthyloxy)-benzonitrile (cf. Example 1), 19.8 g (71 mmol) of dimethyl sulphate, 21.7 g (71 mmol) of potassium carbonate and 200 ml of acetone is stirred and heated under reflux for 20 hours. After cooling to room temperature, the mixture is concentrated under water-pump vacuum, the residue is shaken with ethyl acetate/1N hydrochloric acid and the organic phase is separated off, washed with water, dried with sodium sulphate and filtered. The filtrate is concentrated under water-pump vacuum, the residue is digested with diethyl ether/petroleum ether and the resulting crystalline product is isolated by filtration with suction and purified by column chromatography (silica gel, chloroform/ethyl acetate, vol. 3:1).

This gives (as first fraction) 5-fluoro-2-(5-methoxy-1-naphthyloxy)-4-(3-methyl-2,6-dioxo-4-trifluoromethyl-3,6-dihydro-1(2H)-pyrimidinyl)-benzonitrile of melting point 109° C.

Example 3

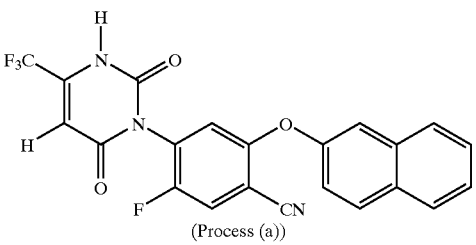

(Process (a))

3.63 g (25 mmol) of 2-naphthol are initially charged in 100 ml of dimethyl sulphoxide and admixed with 2.5 g (25 mmol) of sodium hydride (60%), and the mixture is stirred for 30 minutes. 8.0 g (25 mmol) of 1-(4-cyano-2,5-difluoro-phenyl)-4-trifluoromethyl-3,6-dihydro-2,6-dioxo-1(2H)-pyrimidine are then added and the reaction mixture is stirred at from 60° C. to 70° C. for 20 hours and then poured into about the same amount of 2N hydrochloric acid. The resulting crystalline product is isolated by filtration with suction.

This gives 9.6 g (86% of theory) of 4-(2,6-dioxo-4-trifluoromethyl-3,6-dihydro-1(2H)-pyrimidinyl)-5-fluoro-2-(2-naphthyloxy)benzonitrile of melting point 92° C.

Example 4

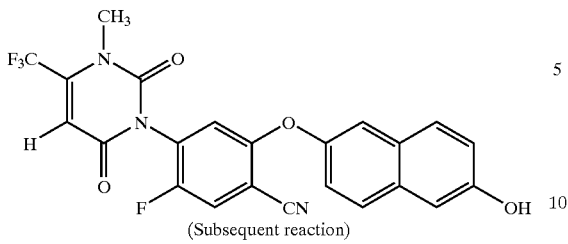

(Subsequent reaction)

A mixture of 2.7 g (5.91 mmol) of 4-(2,6-dioxo-4-trifluoromethyl-3,6-dihydro-1(2H)-pyrimidinyl)-5-fluoro-2-(6-hydroxy-2-naphthyloxy)benzonitrile, 0.89 g (5.91 mmol) of dimethyl sulphate, 0.98 g (5.91 mmol) of potassium carbonate and 100 ml of acetone is stirred and heated under reflux for 20 hours. After cooling to room temperature, the mixture is concentrated under water-pump vacuum, the residue is shaken with ethyl acetate/1N hydrochloric acid and the organic phase is separated off, washed with water, dried with sodium sulphate and filtered. The residue is digested with diethyl ether/petroleum ether and the resulting crystalline product is isolated by filtration with suction and purified by column chromatography (silica gel, chloroform/ethyl acetate,. vol. 2:1).

This gives (as second fraction) 0.8 g (29% of theory) of 5-fluoro-2-(6-hydroxy-2-naphthyloxy)-4-(3-methyl-2,6-dioxo-4-trifluoromethyl-3,6-dihydro-1(2H)-pyrimidinyl)-benzonitrile of melting point 174° C.

Example 5

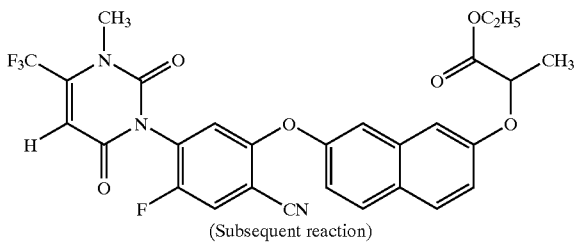

(Subsequent reaction)

A mixture of 0.25 g (0.53 mmol) of 5-fluoro-2-(7-hydroxy-2-naphthyloxy)-4-(3-methyl-2,6-dioxo-4-trifluoromethyl-3,6-dihydro-1(2H)-pyrimidinyl)-benzonitrile, 0.11 g (0.53 mmol) of ethyl 2-bromopropanoate (racemic), 0.10 g (0.53 mmol) of potassium carbonate and 30 ml of acetonitrile is stirred and heated under reflux for 18 hours. After cooling to room temperature, the mixture is concentrated under water-pump vacuum, the residue is shaken with ethyl acetate/1N hydrochloric acid and the organic phase is separated off, washed with saturated aqueous sodium chloride solution, dried with sodium sulphate and filtered. The filtrate is concentrated under water-pump vacuum, the residue is digested with diethyl ether and the resulting crystalline product is isolated by filtration with suction.

This gives 0.15 g (50% of theory) of ethyl 2-[7-(2-cyano4-fluoro-5-[3-methyl-2,6-dioxo-4-trifluoromethyl-3,6-dihydro-1(2H)-pyrimidinyl]-phenoxy)-2-naphthyloxy]-propanoate (racemate) of melting point 133° C.

Example 6

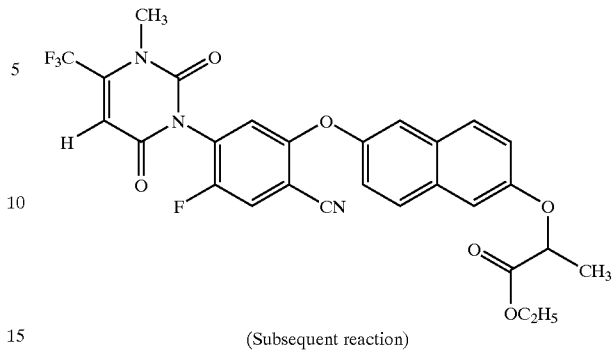

(Subsequent reaction)

A mixture of 0.35 g (0.74 mmol) of 5-fluoro-2-(6-hydroxy-2-naphthyloxy)-4-(3-methyl-2,6-dioxo-4-trifluoromethyl-3,6-dihydro-1(2H)-pyrimidinyl)-benzonitrile, 0.22 g (0.74 mmol) of ethyl (R)-2-(p-tolyl-sulphonyloxy)-propanoate, 0.13 g (0.74 mmol) of potassium carbonate and 30 ml of acetonitrile is stirred and heated under reflux for 20 hours. After cooling to room temperature, the mixture is concentrated under water-pump vacuum, the residue is shaken with ethyl acetate/1N hydrochloric acid and the organic phase is separated off, washed with saturated aqueous sodium chloride solution, dried with sodium sulphate and filtered. The filtrate is concentrated under water-pump vacuum and the residue is purified by column chromatography (silica gel, chloroform/ethyl acetate, vol. 2:1).

This gives 0.06 g (14% of theory) of ethyl (R)-2-[6-(2-cyano-4-fluoro-5-[3-methyl-2,6-dioxo-4-trifluoromethyl-3,6-dihydro-1(2H)-pyrimidinyl]-phenoxy)-2-naphthyl-oxy]-propanoate as an amorphous product (logP:3.99 at pH 2.3)

Analogously to Examples 1 to 6 and in accordance with the general description of the preparation process according to the invention, it is also possible to prepare, for example, the compounds of the general formula (I) listed in the tables below.

(I)

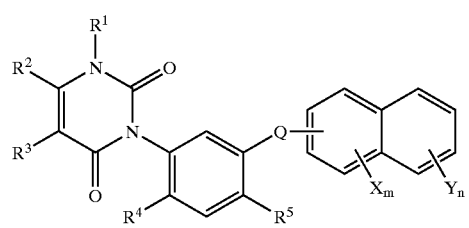

Table 1: Examples of the compounds of the formula (I)

All examples in Table 1 refer to compounds in which Q represents O (oxygen) and $R^3$ represents H (hydrogen).

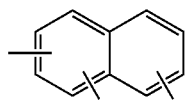

| Ex. No. | Q | R¹ | R² | R³ | R⁴ | R⁵ | (naphthyl group) | Physical Data |
|---|---|---|---|---|---|---|---|---|
| 7 | O | CH₃ | CF₃ | H | F | CN | 5-methyl-1-naphthol | m.p.: 114° C. |
| 8 | O | CH₃ | CF₃ | H | F | CN | ethyl 2-((5-methylnaphthalen-1-yl)oxy)propanoate | m.p.: 126° C. (racemate) |
| 9 | O | H | CF₃ | H | F | CN | 7-methoxy-2-naphthyl (with CH₃ substitution) | m.p.: 76° C. |
| 10 | O | CH₃ | CF₃ | H | F | CN | ethyl 2-((5-methylnaphthalen-1-yl)oxy)acetate | m.p.: 168° C. |
| 11 | O | CH₃ | CF₃ | H | F | CN | 7-methoxynaphthyl | m.p.: 205° C. |
| 12 | O | H | CF₃ | H | F | CN | 6-hydroxynaphthyl | m.p.: 275° C. |
| 13 | O | CH₃ | CF₃ | H | F | CN | 6-hydroxynaphthyl | m.p.: 161° C. |
| 14 | O | CH₃ | CF₃ | H | F | CN | 6-methoxynaphthyl | m.p.: 136° C. |

-continued
| Ex. No. | Q | R¹ | R² | R³ | R⁴ | R⁵ | 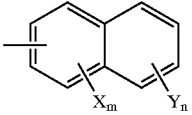 | Physical Data |
|---|---|---|---|---|---|---|---|---|
| 15 | O | H | CF₃ | H | F | CN | 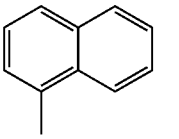 | (amorphous) |
| 16 | O | CH₃ | CF₃ | H | F | CN | 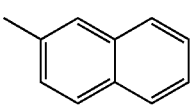 | m.p.: 152° C. |
| 17 | O | H | CF₃ | H | F | CN | 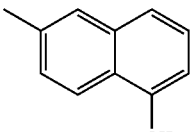 | m.p.: 158° C. |
| 18 | O | CH₃ | CF₃ | H | F | CN | 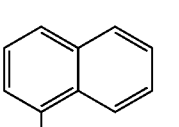 | m.p.: 142° C. |
| 19 | O | CH₃ | CF₃ | H | F | CN | 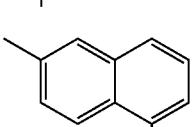 | m.p.: 130° C. |
| 20 | O | CH₃ | CF₃ | H | F | CN | 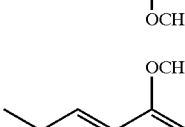 | m.p.: 152° C. |
| 21 | O | CH₃ | CF₃ | H | F | CN | 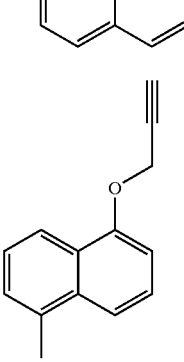 | |
| 22 | O | CH₃ | CF₃ | H | F | CN | 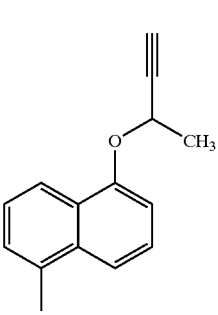 | |

-continued
| Ex. No. | Q | R¹ | R² | R³ | R⁴ | R⁵ | 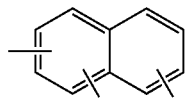 | Physical Data |
|---|---|---|---|---|---|---|---|---|
| 23 | O | CH₃ | CF₃ | H | F | CN | 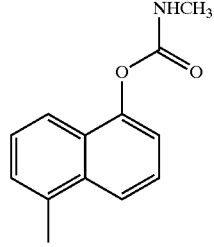 | m.p.: 164° C. |
| 24 | O | CH₃ | CF₃ | H | F | CN | 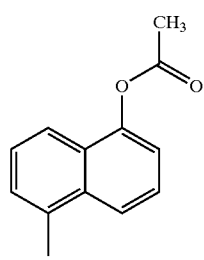 | |
| 25 | O | CH₃ | CF₃ | H | F | CN | 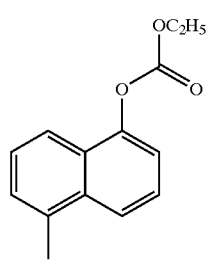 | |
| 26 | O | CH₃ | CF₃ | H | F | CN | 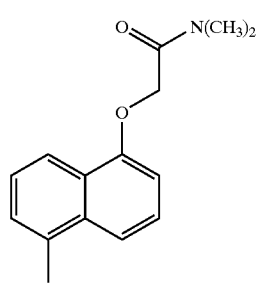 | m.p.: 225° C. |
| 27 | O | CH₃ | CF₃ | H | F | CN | 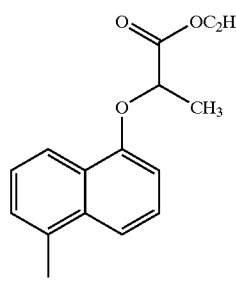 | m.p.: 151° C. (racemate) |

-continued

| Ex. No. | Q | R¹ | R² | R³ | R⁴ | R⁵ | (naphthyl group) | Physical Data |
|---|---|---|---|---|---|---|---|---|
| 28 | O | $CH_3$ | $CF_3$ | H | F | CN | 5-methyl-naphthalen-1-yl-O-CH($CH_3$)-C(O)-NHC$_6$H$_5$ | |
| 29 | O | $CH_3$ | $CF_3$ | H | F | CN | 5-methyl-naphthalen-1-yl-O-CH($CH_3$)-C(O)-OC$_2$H$_5$ | (R enantiomer) |
| 30 | O | $CH_3$ | $CF_3$ | H | F | CN | 7-methyl-1-hydroxy-naphthalene | m.p.: 155° C. |
| 31 | O | H | OH, C(O) | H | F | CN | 6-methyl-2-methoxy-naphthalene | logP = 2.11[a] |
| 32 | O | H | OH, C(O) | H | F | CN | 7-methyl-2-methoxy-naphthalene | logP = 2.13[a] |
| 33 | O | $CH_3$ | OCH$_3$, C(O) | H | F | CN | 6-methyl-2-methoxy-naphthalene | logP = 3.22[a] |
| 34 | O | $CH_3$ | OCH$_3$, C(O) | H | F | CN | 7-methyl-2-methoxy-naphthalene | logP = 3.26[a] |
| 35 | O | $CH_3$ | NH$_2$, C(O) | H | F | CN | 6-methyl-2-methoxy-naphthalene | logP = 2.06[a] |
| 36 | O | H | $CF_3$ | H | F | CN | 7-methyl-2-hydroxy-naphthalene | m.p.: 156° C. |

-continued

| Ex. No. | Q | R¹ | R² | R³ | R⁴ | R⁵ | naphthyl group | Physical Data |
|---|---|---|---|---|---|---|---|---|
| 37 | O | H | $CF_3$ | H | F | CN | 1-Cl, 4-yl naphthyl | m.p.: 118° C. |
| 38 | O | H | $CF_3$ | H | F | CN | 1-OH, 4-yl naphthyl | m.p.: 96° C. |
| 39 | O | $CH_3$ | $CF_3$ | H | F | CN | 1-$OCH_3$, 4-yl naphthyl | m.p.: 144° C. |
| 40 | O | $CH_3$ | $CF_3$ | H | F | CN | 6-methyl-1-($CO_2CH_3$) naphthyl | m.p.: 131° C. |
| 41 | O | $CH_3$ | $CF_3$ | H | F | CN | 1-OH, 4-yl naphthyl | m.p.: 134° C. |
| 42 | O | $CH_3$ | $CF_3$ | H | F | CN | 1-OH, 4-yl naphthyl | m.p.: 164° C. |
| 43 | O | $CH_3$ | $CF_3$ | H | F | CN | 1-[OCH($CH_3$)$CO_2C_2H_5$]-5-yl naphthyl | m.p.: 118° C. |

-continued

| Ex. No. | Q | R¹ | R² | R³ | R⁴ | R⁵ | Xₘ / Yₙ (naphthalene) | Physical Data |
|---------|---|-----|-----|-----|-----|-----|-----------------------|---------------|
| 44 | O | CH₃ | CN | H | F | CN | 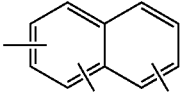 | logP = 3.21[a] |
| 45 | O | CH₃ | 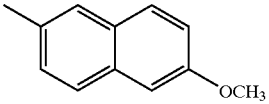 | H | F | CN |  | logP = 2.43[a] |
| 46 | O | CH₃ | CN | H | F | CN | 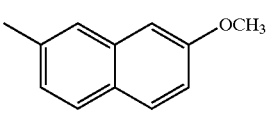 | logP = 2.24[a] |

The logP values given in Table 1 were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqeuous phosphoric acid, acetonitrile; linear gradient from 10% acetonitrile to 90% acetonitrile—the corresponding test results in Table 1 are labelled[a]).

(b) Mobile phases for the determination in the neutral range: 0.01 molar aqueous phosphate buffer solution, acetonitrile; linear gradient from 10% acetonitrile to 90% acetonitrile—the corresponding test results in Table 1 are labelled[b]).

Calibration was carried out using unbranched alkan-2-ones (having 3 to 16 carbon atoms) with known logP values (determination of the logP values by the retention times using linear interpolation between two successive alkanones).

The lambda-max values were determined using the UV spectra from 200 nm to 400 nm in the maxima of the chromatographic signals.

The compound listed above in Table 1 as Example 31 can be prepared, for example, as follows:

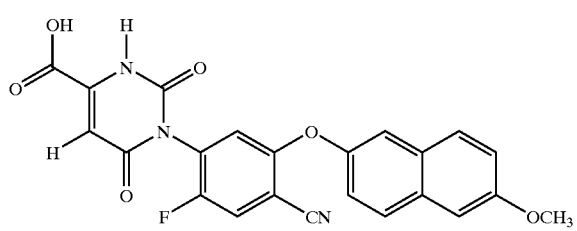

13.0 g (27.4 mmol) of ethyl [1-(4-cyano-2-fluoro-5-(6-methoxy-naphthalen-2-yl-oxy)-phenyl)-2,5-dioxo-2,5-dihydro-1H-pyrrol-3-yl]-carbamate are dissolved in 200 ml of 1,4-dioxane, and a solution of 1.2 g (30 mmol) of sodium hydroxide in 40 ml of water is added dropwise with stirring at room temperature (about 20° C.). The reaction mixture is then stirred at 90° C. for 4 hours and subsequently concentrated under water-pump vacuum. The residue is taken up in 800 ml of water and acidified using conc. hydrochloric acid. The resulting crystalline product is isolated by filtration with suction.

This gives 11.8 g (96% of theory) of 1-[4-cyano-2-fluoro-5-(6-methoxy-naphthalen-2-yl-oxy)-phenyl]-2,6-dioxo-1,2,3,6-tetrahydro-pyrimidine-4-carboxylic acid.

The compound listed above in Table 1 as Example 33 can be prepared, for example, as follows:

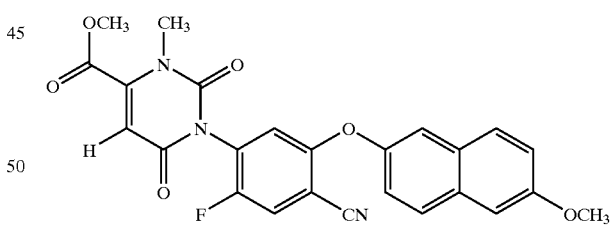

11.5 g (25.7 mmol) of 1-[4-cyano-2-fluoro-5-(6-methoxy-naphthalen-2-yl-oxy)-phenyl]-2,6-dioxo-1,2,3,6-tetrahydro-pyrimidine4-carboxylic acid are initially charged in 200 ml of acetone and admixed with 7.8 g (56 mmol) of potassium carbonate. At room temperature (about 20° C.), a solution of 8.1 g (64 mmol) of dimethyl sulphate in 20 ml of acetone is then added dropwise with stirring, and the reaction mixture is heated under reflux for 4 hours. The mixture is subsequently concentrated under water-pump vacuum, the residue is taken up in 600 ml of water and acidified with conc. hydrochloric acid and the resulting crystalline product is isolated by filtration with suction.

This gives 11 g (90% of theory) of methyl I-[4-cyano-2-fluoro-5-(6-methoxy-naphthalen-2-yl-oxy)-phenyl]-2,6-dioxo-3-methyl- 1,2,3,6-tetrahydro-pyrimidine-4-carboxylate.

The compound listed above in Table 1 as Example 35 can be prepared, for example, as follows:

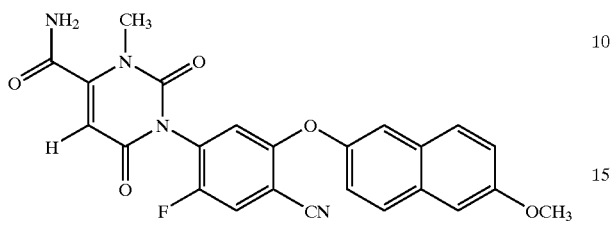

10.7 g (22.5 mmol) of methyl 1-[4-cyano-2-fluoro-5-(6-methoxy-naphthalen-2-yl-oxy)-phenyl]-2,6-dioxo-3-methyl- 1,2,3,6-tetrahydro-pyrimidine-4-carboxylate are dissolved in 200 ml of tetrahydrofuran and admixed successively with 10.3 g of ammonium chloride and a 25% strength aqueous ammonia solution. The reaction mixture is stirred at room temperature (about 20° C.) for 12 hours and subsequently concentrated under water-pump vacuum. The residue is stirred with hexane and the crystalline product is isolated by filtration with suction.

This gives 9.4 g (91% of theory) of 1-[4-cyano-2-fluoro-5-(6-methoxy-naphthalen-2-yl-oxy)-phenyl]-2,6-dioxo-3-methyl-1,2,3,6-tetrahydro-pyrimidine4-carboxamide.

PRECURSORS OF THE FORMULA (VI)

Example (VI-1)

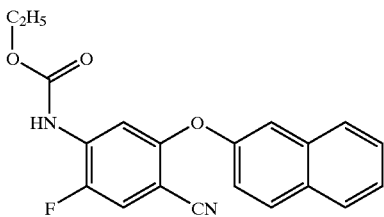

2.0 g (7.2 mmol) of 4-amino-5-fluoro-2-(2-naphthyloxy)-benzonitrile are initially charged in 100 ml of acetone and, at 40° C., admixed dropwise with stirring with 1.78 g (7.2 mmol) of trichloromethyl chloroformate ("diphosgene"). The reaction mixture is stirred at 40° C. for 4 hours and then added dropwise with stirring to 100 ml of ethanol. The mixture is then stirred at room temperature (about 20° C.) for 15 minutes and subsequently concentrated under water-pump vacuum. The residue is stirred with diethyl ether/petroleum ether and the resulting crystalline product is isolated by filtration with suction.

This gives 0.4 g (16% of theory) of O-ethyl N-[4-cyano-2-fluoro-5-(2-naphthyloxy)-phenyl]-carbamate of melting point 132° C.

PRECURSORS OF THE FORMULA (VII):

Example (VII-1)

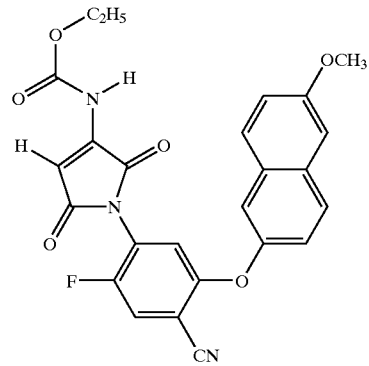

A mixture of 15.0 g (48.7 mmol) of 4-amino-5-fluoro-2-(6-methoxy-naphthalen-2-yl-oxy)-benzonitrile, 10.8 g (58 mmol) of ethyl (2,5-dioxo-2,5-dihydro-furan-3-yl)-carbamate and 200 ml of acetic acid is heated under reflux for 4 hours and subsequently concentrated under water-pump vacuum. The residue is stirred with water and the crystalline product is isolated by filtration with suction and purified by column chromatography (silica gel, methylene chloride/ethyl acetate, vol. 95/5).

This gives 13.5 g (58% of theory) of ethyl [1-(4-cyano-2-fluoro-5-(6-methoxy-naphthalen-2-yl-oxy)-phenyl)-2,5-dioxo-2,5-dihydro- 1H-pyrrol-3-yl]-carbamate. logP=3.63)

Analogously to Example (VII-1), it is also possible to prepare, for example, the compounds of the general formula (VII) listed in Table 2 below.

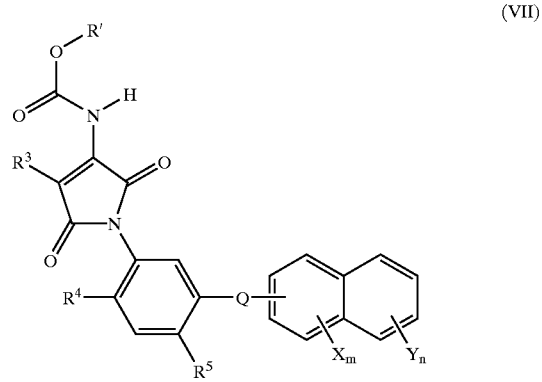

(VII)

TABLE 2

Examples of the compounds of the formula (VII)

| Ex. No. | Q | $R^2$ | $R^3$ | $R^4$ | $R^5$ | $X_m$ | $Y_n$ | Physical Data |
|---|---|---|---|---|---|---|---|---|
| VII-2 | O | $C_2H_5$ | H | F | CN | 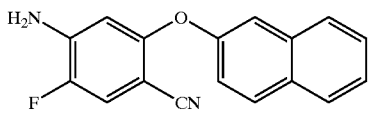 OCH₃ | | logP = 3.67[a)] |
| VII-2 | O | $C_2H_5$ | H | F | CN | | | |
| VII-3 | O | $C_2H_5$ | H | F | CN | | | |
| VII-4 | O | $C_2H_5$ | H | F | CN | | | |

PRECURSORS OF THE FORMULA (IX)

Example (IX-1)

3.93 g (26 mmol) of 2-naphthol are initially charged in 150 ml of N-methyl-pyrrolidone and mixed with 1.25 g (26 mmol) of sodium hydride (60%), and the mixture is stirred at room temperature (about 20° C.) for 30 minutes and then admixed with 4.0 g (26 mmol) of 4-amino-2,5-difluoro-benzonitrile and stirred at from 105° C. to 115° C. for two days. After cooling to room temperature, the mixture is poured into about the same amount of 2N hydrochloric acid, stirred for 15 minutes and extracted with ethyl acetate. The organic phase is washed with water, dried with sodium sulphate and filtered. The filtrate is concentrated under water-pump vacuum, the residue is digested with diethyl ether/petroleum ether and the crystalline product is isolated by filtration with suction and purified by column chromatography (silica gel, chloroform/ethyl acetate, vol. 4:1).

This gives 1.0 g (14% of theory) of [4]-amino-5-fluoro-2-(2-naphthyloxy)-benzonitrile of melting point 89° C.

Analogously to Example (IX-1), it is also possible to prepare, for example, the compounds of the general formula (IX) listed in Table 3 below.

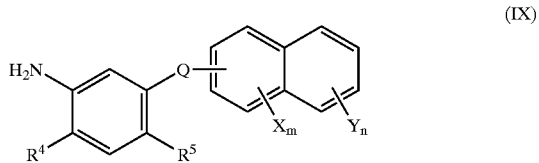

(IX)

TABLE 3

Examples of the compounds of the formula (IX)

| Ex. No. | Q | $R^4$ | $R^5$ | $X_m$ | $Y_n$ | Physical Data |
|---|---|---|---|---|---|---|
| IX-2 | O | F | CN | OH (naphthyl) | | ¹H-NMR (D₆-DMSO, δ): 8.03, 8.06 ppm |
| IX-3 | O | F | CN | OCH₃ (naphthyl) | | m.p.: 130° C. |

TABLE 3-continued

Examples of the compounds of the formula (IX)

| Ex. No. | Q | R⁴ | R⁵ | $X_m$ | $Y_n$ | Physical Data |
|---|---|---|---|---|---|---|
| IX-4 | O | F | CN | 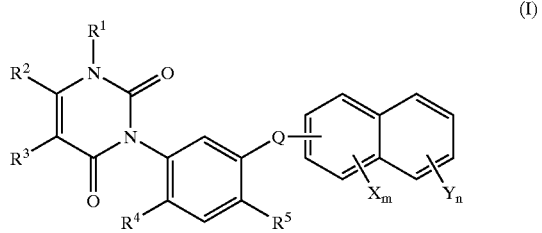 | | m.p.: 144° C. |

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 litres of water per hectare.

After three weeks the degree of damage to the plants is rated in % damage in comparison to the development of the untreated control.

The figures denote:

0%=no effect (like untreated control)

100%=total destruction

In this test, for example, the compounds of Preparation Examples 7, 8, 10, 11 and 13 exhibit strong activity against weeds, and some of them are tolerated well by crop plants, such as, for example, maize.

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of preparation examples 7, 8, 10, 11 and 13 exhibit strong activity against weeds.

What is claimed:

1. A phenyluracil of the Formula (I)

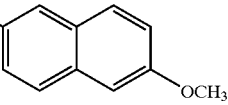

m represents 0, 1 or 2, n represents 0, 1, 2 or 3,

Q represents O (oxygen), S (sulphur), SO, SO₂, NH or N(C₁–C₄-alkyl),

R¹ represents hydrogen, amino or represents optionally cyano-, halogen- or C₁–C₃-alkoxy-substituted alkyl having 1 to 4 carbon atoms, R² represents carboxyl, cyano, carbamoyl, thiocarbamoyl or represents in each case optionally cyano-, halogen- or C₁–C₃-alkoxy-substituted alkyl or alkoxycarbonyl having in each case 1 to 4 carbon atoms, R³ represents hydrogen, halogen or represents optionally cyano-, halogen- or C₁–C₃-alkoxy-substituted alkyl having 1 to 4 carbon atoms, R⁴ represents hydrogen, cyano, fluorine or chlorine, R⁵ represents cyano, carbamoyl, thiocarbamoyl, halogen or represents in each case optionally halogen-substituted alkyl or alkoxy having in each case 1 to 4 carbon atoms, X represents hydroxyl, mercapto, amino, nitro, formyl, cyano, carboxyl, carbamoyl, thiocarbamoyl, halogen, sulphonyl, halogenosulphonyl, represents optionally unsubstituted or cyano-, carboxyl-, carbamoyl-, halogen-, C₁–C₄-alkoxy-, C₁–C₄-alkylthio-, C₁–C₄-alkylsulphinyl-, C₁–C₄-alkylsulphonyl-, C₁–C₄-alkylcarbonyl-, C₁–C₄-alkoxy-carbonyl-, C₂–C₄-alkenyloxy-carbonyl-, C₂–C₄-alkinyloxy-carbonyl-, C₁–C₄-alkylamino-carbonyl-, di-(C₁–C₄-alkyl)-amino-carbonyl-, phenoxycarbonyl-, benzyloxycarbonyl-, phenylaminocarbonyl- or benzylaminocarbonyl- substituted alkyl, alkoxy, alkylthio, alkylsulphinyl, alkylsulphonyl or alkylamino having in each case 1 to 6 carbon atoms, represents dialkylamino, alkylcarbonyl, alkoxycarbonyl, alkylaminocarbonyl, dialkylaminocarbonyl, alkylcarbonyloxy, alkoxycarbonyloxy, alkylamino-carbonyloxy, dialkylaminocarbonyloxy, alkylcarbonylamino, alkoxy-carbonylamino, alkylsulfonylamino, bis-alkylsulfonyl-amino or N-alkyl-carbonyl-N-alkylsulphonyl-amino having in each case 1 to 6 carbon atoms in the alkyl groups, represents optionally unsubstituted or cyano-, carboxyl-, carbamoyl-, halogen-, $C_1$–$C_4$-alkoxy-carbonyl-, $C_1$–$C_4$-alkylamino-carbonyl- or di-($C_1$–$C_4$-alkyi )-amino-carbonyl-substituted alkenyl, alkenyloxy, alkenyloxycarbonyl, alkenylcarbonyloxy, alkinyl, alkinyloxy, alkinyloxycarbonyl or alkinylcarbonyloxy having in each case 2 to 6 carbon atoms in the alkenyl or alkinyl groups, or represents benzyloxy, and Y represents hydroxyl, mercapto, amino, nitro, formyl, cyano, carboxyl, carbamoyl, thiocarbamoyl, halogen, sulphonyl, halogenosulphonyl, represents optionally unsubstituted or cyano-, carboxyl-, carbamoyl-, halogen-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkylcarbonyl-, $C_1$–C4-alkoxy-carbonyl-, $C_2$–$C_4$-alkenyloxy-carbonyl-, $C_2$–$C_4$-alkinyloxy-carbonyl-, amino-carbonyl-, $C_1$–$C_4$-alkylaminocarbonyl-, di-($C_1$–$C_4$-alkyl)-amino-carbonyl-, phenoxycarbonyl-, benzyloxycarbonyl-, phenylaminocarbonyl- or benzylaminocarbonyl-substituted alkyl, alkoxy, alkylthio, alkylsulphinyl, alkylsulphonyl or alkylamino having in each case 1 to 6 carbon atoms, represents dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, alkylcarbonylamino, alkoxycarbonylamino, alkylsulfonylamino, bis-alkylsulfonyl-amino or N-alkylcarbonyl-N-alkylsulphonyl-amino having in each case 1 to 6 carbon atoms in the alkyl groups, represents optionally unsubstituted or cyanocarboxyl-, carbamoyl-, halogen-, $C_1$–$C_4$-alkoxycarbonyl-, $C_1$–$C_4$-alkylamino-carbonyl- or di-($C_1$–$C_4$-alkyl )-amino-carbonyl-substituted alkenyl, alkenyloxy, alkenyloxycarbonyl, alkenylcarbonyloxy, alkinyl, alkinyloxy, alkinyloxycarbonyl or alkinylcarbonyloxy having in each case 2 to 6 carbon atoms in the alkenyl or alkinyl groups, or represents benzyloxy, where, in the case that m and/or n are greater than 1, X and Y are identical or different, or salts of compounds of the Formula (I).

2. A phenyluracil according to claim 1 wherein m represents 0 or 1, n represents 0, 1 or 2, Q represents O (oxygen) or S (sulphur), $R^1$ represents hydrogen, amino or represents in each case optionally cyano-, fluorine-, chlorine-, methoxy- or ethoxy-substituted methyl, ethyl, n- or i-propyl, $R^2$ represents carboxyl, cyano, carbamoyl, thiocarbamoyl or represents in each case optionally cyano-, fluorine-, chlorine-, methoxy- or ethoxy-substituted methyl, ethyl, n- or i-propyl, methoxycarbonyl, ethoxycarbonyl, n- or i-propoxycarbonyl, $R^3$ represents hydrogen, fluorine, chlorine, bromine, or represents in each case optionally cyano-, fluorine-, chlorine-, methoxy- or ethoxy-substituted methyl, ethyl, n- or i-propyl, $R^4$ represents hydrogen, fluorine or chlorine, $R^5$ represents cyano, carbamoyl, thiocarbamoyl, fluorine, chlorine, bromine, or represents in each case optionally fluorine- and/or chlorine-substituted methyl, ethyl, n- or i-propyl, methoxy, ethoxy, n- or i-propoxy, X represents hydroxyl, mercapto, amino, nitro, formyl, cyano, carboxyl, carbamoyl, thiocarbamoyl, fluorine, chlorine, bromine, sulphonyl, chlorosulphonyl, represents optionally unsubstituted or cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-, acetyl-, propionyl-, n- or i-butyroyl-, methoxycarbonyl-, ethoxycarbonyl-, n- or i-propoxycarbonyl-, n-, i-, s- or t-butoxycarbonyl-, propenyloxycarbonyl-, butenyloxycarbonyl-, propinyloxycarbonyl-, butinyloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl-substituted methyl, ethyl, n- or i-propyl, methoxy, ethoxy, n- or i-propoxy, methylthio, ethylthio, n- or i-propylthio, methyl-sulphinyl, ethylsulphinyl, n- or i-propylsulphinyl, methylsulphonyl, ethylsulphonyl, n- or i-propylsulphonyl, methylamino, ethylamino, n- or i-propylamino, represents dimethylamino, diethylamino, acetyl, propionyl, n- or i-butyroyl, methoxycarbonyl, ethoxycarbonyl, n- or i-propoxycarbonyl, methylaminocarbonyl, ethylaminocarbonyl, n- oder i-propylaminocarbonyl, dimethylaminocarbonyl, diethylaminocarbonyl, acetyloxy, propinoyloxy, n- or i-butyroyloxy, methoxycarbonyloxy, ethoxycarbonyloxy, n- or i-propoxycarbonyloxy, n-, i-, s- or t-butoxycarbonyloxy, methylaminocarbonyloxy, ethylaminocarbonyloxy, n- or i-propylaminocarbonyloxy, n-, i-, s- or t-butylaminocarbonyloxy, dimethyl-aminocarbonyloxy, diethylaminocarbonyloxy, acetylamino, propionylamino, n- or i-butyroylamino, methoxycarbonylamino, ethoxy-carbonylamino, n- or i-propoxycarbonylamino, methylsulphonylamino, ethylsulphonylamino, n- or i-propylsulphonylamino, or represents optionally unsubstituted or cyano-, carboxyl-, carbamoyl-, fluorine-, chlorine-, bromine-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylamino-carbonyl-substituted ethenyl, propenyl, butenyl, propenyloxy, butenyloxy, propenyloxycarbonyl, butenyloxycarbonyl, ethenecarbonyloxy, propenecarbonyloxy, butenecarbonyloxy, ethinyl, propinyl, butinyl, propinyloxy, butinyloxy, propinyloxycarbonyl, butinyloxycarbonyl, ethinecarbonyloxy, propinecarbonyloxy or butinecarbonyloxy, or represents benzoyloxy, Y represents hydroxyl, mercapto, amino, nitro, formyl, cyano, carboxyl, carbamoyl, thiocarbamoyl, fluorine, chlorine, bromine, sulphonyl, chlorosulphonyl, represents optionally unsubstituted or cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-, acetyl-, propionyl-, n- or i-butyroyl-, methoxycarbonyl-, ethoxycarbonyl-, n- or i-propoxycarbonyl-, n-, i-, s- or t-butoxycarbonyl-, propenyloxycarbonyl-, butenyloxycarbonyl-, propinyloxycarbonyl-, butinyloxycarbonyl-, aminocarbonyl-, methylaminocarbonyl-, ethylaminocarbonyl-, n- or i-propylaminocarbonyl-, dimethylaminocarbonyl-, diethylaminocarbonyl-, phenylaminocarbonyl- or benzylaminocarbonyl-substituted methyl, ethyl, n- or i-propyl, methoxy, ethoxy, n- or i-propoxy, methylthio, ethylthio, n- or i-propylthio, methylsulphinyl, ethylsulphinyl, n- or i-propyl-sulphinyl, methylsulphonyl, ethylsulphonyl, n- or i-propylsulphonyl, methylamino, ethylamino, n- or i-propylamino, represents dimethylamino, diethylamino, acetyl, propionyl, n- or i-butyroyl, methylcarbonyloxy, methoxycarbonyl, ethoxycarbonyl, n- or i-propoxycarbonyl, methylaminocarbonyl, ethylaminocarbonyl, n- or i-propylaminocarbonyl, dimethylaminocarbonyl, diethylaminocarbonyl, acetyloxy, propinoyloxy, n- or i-butyroyloxy, methylcarbonyloxy, methoxycarbonyloxy, ethoxycarbonyloxy, n- or i-propoxycarbonyloxy, n-, i-, s- or t-butoxycarbonyloxy, methylaminocarbonyloxy, ethylamino-carbonyloxy, n- or i-propyl-aminocarbonyloxy, n-, i-, s- or t-butylamino-carbonyloxy, dimethylaminocarbonyloxy, diethylaminocarbonyloxy, acetylamino, propionylamino, n- or i-butyroylamino, methoxycarbonyl-amino, ethoxycarbonylamino, n- or i-propoxycarbonylamino, methyl-sulphonylamino, ethylsulphonylamino, n- or i-propylsulphonylamino, or represents optionally unsubstituted or cyano-, carboxyl-, carbamoyl-, fluorine-, chlorine-, bromine-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylamino-carbonyl-substituted ethenyl, propenyl, butenyl, propenyloxy, butenyloxy, propenyloxycarbonyl, butenyl-oxycarbonyl, ethenecarbonyloxy, propenecarbonyloxy, butenecarbonyloxy, ethinyl, propinyl, butinyl, propinyloxy, butinyloxy, propinyloxycarbonyl, butinyloxycarbonyl, ethinecarbonyloxy, propinecarbonyloxy or butinecarbonyloxy, or represents benzoyloxy.

3. A phenyluracil according to claim 1 wherein m represents 0, n represents 0 or 1, Q represents O (oxygen), $R^1$ represents hydrogen, amino or methyl, $R^2$ represents carboxyl, cyano, carbamoyl, thiocarbamoyl or represents in each case optionally fluorine- and/or chlorine-substituted methyl, ethyl, methoxycarbonyl or ethoxycarbonyl, $R^3$ represents hydrogen, fluorine, chlorine, bromine, or represents optionally fluorine- and/or chlorine-substituted methyl, $R^4$ represents fluorine, $R^5$ represents cyano, carbamoyl, thiocarbamoyl, fluorine, chlorine, bromine, or represents in each case optionally fluorine- and/or chlorine-substituted methyl or methoxy, X represents hydroxyl, mercapto, amino, nitro, formyl, cyano, carboxyl, carbamoyl, thiocarbamoyl, fluorine, chlorine, bromine, sulphonyl, chlorosulphonyl, represents optionally unsubstituted or cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, propenyloxycarbonyl-, methylaminocarbonyl-, ethylaminocarbonyl-, n- or i-propylamino-carbonyl-, dimethylaminocarbonyl- or benzyloxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methyl-sulphonyl, ethylsulphonyl, methylamino, ethylamino, n- or i-propyl-amino, represents dimethylamino, diethylamino, acetyl, propionyl, n- or i-butyroyl, methoxycarbonyl, ethoxycarbonyl, n- or i-propoxycarbonyl, methylaminocarbonyl, ethylaminocarbonyl, n- oder i-propylamino-carbonyl, dimethylaminocarbonyl, diethylaminocarbonyl, acetyloxy, propinoyloxy, n- or i-butyroyloxy, methoxycarbonyloxy, ethoxycarbonyloxy, n- or i-propoxycarbonyloxy, methylaminocarbonyloxy, ethylamino-carbonyloxy, n- or i-propyl-aminocarbonyloxy, dimethylaminocarbonyloxy, diethylaminocarbonyloxy, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, or represents optionally unsubstituted or cyano-, carboxyl-, carbamoyl-, fluorine-, chlorine-, bromine-, methoxycarbonyl-, ethoxycarbonyl-, n- or i-propoxycarbonyl-, methylaminocarbonyl-, ethylaminocarbonyl-, n- or i-propylaminocarbonyl-, dimethyl-aminocarbonyl- or diethylaminocarbonyl-substituted ethenyl, propenyl, butenyl, propenyloxy, butenyloxy, propenyloxycarbonyl, butenyloxycarbonyl, ethinyl, propinyl, butinyl, propinyloxy, butinyloxy, propinyloxy-carbonyl or butinyloxycarbonyl, or represents benzoyloxy, and Y represents hydroxyl, mercapto, amino, nitro, formyl, cyano, carboxyl, carbamoyl, thiocarbamoyl, fluorine, chlorine, bromine, sulpho, chlorosulphonyl, represents optionally unsubstituted or cyano-, carboxyl-, carbamoyl-, thiocarbamoyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, methylsulphonyl-, ethylsulfonyl-, acetyl-, propionyl-, n- or i-butyroyl-, methoxycarbonyl-, ethoxycarbonyl-, n- or i-propoxycarbonyl-, propenyloxycarbonyl-, aminocarbonyl-, methylaminocarbonyl-, ethylaminocarbonyl-, n- or i-propylaminocarbonyl-, dimethylaminocarbonyl-, phenylaminocarbonyl- or benzyloxycarbonyl-substituted methyl, ethyl, n- or i-propyl, methoxy, ethoxy, n- or i-propoxy, methylthio, ethylthio, n- or i-propylthio, methyl-sulphinyl, ethylsulphinyl, methylsulphonyl, ethylsulphonyl, methylamino, ethylamino, n- oder i-propylamino, represents dimethylamino, diethylamino, acetyl, propionyl, n- or i-butyroyl, methoxycarbonyl, ethoxycarbonyl, n- or i-propoxycarbonyl, methylaminocarbonyl, ethylamino-carbonyl, n- or i-propylaminocarbonyl, dimethylaminocarbonyl, diethyl-aminocarbonyl, acetyloxy, propinoyloxy, n- or i-butyroyloxy, methyl-carbonyloxy, methoxycarbonyloxy, ethoxycarbonyloxy, n- or i-propoxy-carbonyloxy, methylaminocarbonyloxy, ethylaminocarbonyloxy, n- or i-propyl-aminocarbonyloxy, dimethylaminocarbonyloxy, diethylamino-carbonyloxy, acetylamino, propionylamino, n- or i-butyroylamino, methoxycarbonylamino, ethoxycarbonylamino, n- or i-propoxycarbonyl-amino, methylsulphonylamino, ethylsulphonylamino, n- or i-propyl-sulphonylamino, or represents optionally unsubstituted or cyano-, carboxyl-, carbamoyl-, fluorine-, chlorine-, bromine-, methoxycarbonyl-, ethoxycarbonyl-, n- or i-propoxycarbonyl-, methylaminocarbonyl-, ethyl-aminocarbonyl-, n- or i-propylaminocarbonyl-, dimethylaminocarbonyl- or or diethylaminocarbonyl-substituted ethenyl, propenyl, butenyl, propenyloxy, butenyloxy, propenyloxycarbonyl, butenyl-oxycarbonyl, ethinyl, propinyl, butinyl, propinyloxy, butinyloxy, propinyloxycarbonyl or butinyloxycarbonyl, or represents benzoyloxy.

4. A phenyluracil according to claim 1 wherein
   $R^2$ represents trifluoromethyl,
   $R^3$ represents hydrogen, and
   $R^5$ represents cyano.

5. A phenyluracil according to claim 1 wherein
   Q represents oxygen (O).

6. A phenyluracil according to claim 1 wherein
   Y represents hydroxyl, methoxy, represents in each case methoxycarbonyl-, ethoxycarbonyl-, methyl-aminocarbonyl-, dimethyl-aminocarbonyl- and phenylaminocarbonyl-substituted methoxy and ethoxy, represents methylaminocarbonyloxy, methyl-carbonyloxy, propinyloxy, butinyloxy and ethoxycarbonyloxy.

7. A compound of the Formula (Ia)

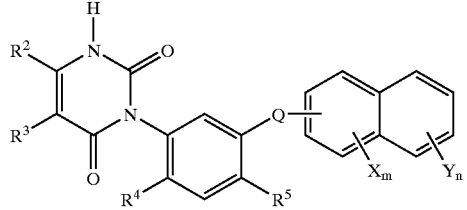

(Ia)

in which
   m, n, Q, $R^2$, $R^3$, $R^4$, $R^5$, X and Y are each as defined in claim 1.

8. An herbicidal composition comprising an effective amount of one or more compounds according to claim 1 and one or more extenders.

9. A method for controlling undesirable plants comprising the step of allowing an effective amount of one or more compounds according to claim 1 to act on a member selected from the group consisting of said undesirable plants, a habitat of said undesirable plants and combinations thereof.

* * * * *